(12) United States Patent
Schindhelm et al.

(10) Patent No.: US 9,597,468 B2
(45) Date of Patent: Mar. 21, 2017

(54) METHODS AND APPARATUS FOR PROVIDING VENTILATION TO A PATIENT

(71) Applicant: ResMed Limited, Bella Vista, New South Wales (AU)

(72) Inventors: Klaus Henry Schindhelm, Glenhaven (AU); Gordon Joseph Malouf, Elizabeth Bay (AU); Steven Paul Farrugia, Lugarno (AU); Clancy John Dennis, McMahons Point (AU); Michael Berthon-Jones, Leonay (AU); David John Bassin, Coogee (AU); Helmut Teschler, Velbert (DE)

(73) Assignee: RedMed Limited (AU)

( * ) Notice: Subject to any disclaimer, the term of this patent is extended or adjusted under 35 U.S.C. 154(b) by 322 days.

(21) Appl. No.: 14/356,471

(22) PCT Filed: Nov. 7, 2012

(86) PCT No.: PCT/AU2012/001367
§ 371 (c)(1),
(2) Date: May 6, 2014

(87) PCT Pub. No.: WO2013/067580
PCT Pub. Date: May 16, 2013

(65) Prior Publication Data
US 2014/0290658 A1 Oct. 2, 2014

(30) Foreign Application Priority Data

Nov. 7, 2011 (AU) .................................. 2011904599
Jun. 15, 2012 (AU) .................................. 2012902501
Jun. 26, 2012 (AU) .................................. 2012902693

(51) Int. Cl.
*A61M 16/00* (2006.01)
*A61B 5/0205* (2006.01)
(Continued)

(52) U.S. Cl.
CPC ....... *A61M 16/0051* (2013.01); *A61B 5/0205* (2013.01); *A61B 5/0488* (2013.01);
(Continued)

(58) Field of Classification Search
CPC ..... A61F 5/56; A61M 16/00; A61M 16/0051; A61M 16/0069; A61M 16/202;
(Continued)

(56) References Cited

U.S. PATENT DOCUMENTS 4,944,310 A 7/1990 Sullivan
5,551,419 A * 9/1996 Froehlich .......... A61M 16/0069
128/204.23
(Continued)

FOREIGN PATENT DOCUMENTS

DE 102007039004 A1 3/2008
NZ 552070 A 11/2008
(Continued)

OTHER PUBLICATIONS

European Search Report for Application No. 12846933.5 dated Jul. 28, 2015.
(Continued)

*Primary Examiner* — Annette Dixon
(74) *Attorney, Agent, or Firm* — Lerner, David, Littenberg, Krumholz & Mentlik, LLP

(57) ABSTRACT

The present technology relates to methods and apparatus to provide ventilation to patients. In particular, the present technology relates to changing ventilator parameters to match changing patient metabolic demand.

33 Claims, 12 Drawing Sheets

(51) Int. Cl.
*A61B 5/0488* (2006.01)
*A61B 5/1455* (2006.01)
*A61B 5/00* (2006.01)
A61M 16/10 (2006.01)
A61M 16/16 (2006.01)
A61B 5/024 (2006.01)
A61B 5/08 (2006.01)
A61B 5/085 (2006.01)
A61B 5/087 (2006.01)

(52) U.S. Cl.
CPC ........ *A61B 5/14551* (2013.01); *A61B 5/4836* (2013.01); *A61B 5/4866* (2013.01); *A61M 16/0006* (2014.02); *A61M 16/0069* (2014.02); *A61M 16/107* (2014.02); *A61B 5/024* (2013.01); *A61B 5/085* (2013.01); *A61B 5/087* (2013.01); *A61B 5/0816* (2013.01); *A61M 16/1075* (2013.01); *A61M 16/16* (2013.01); *A61M 2016/0018* (2013.01); *A61M 2016/0027* (2013.01); *A61M 2016/0033* (2013.01); *A61M 2016/0036* (2013.01); *A61M 2016/0039* (2013.01); *A61M 2205/502* (2013.01); *A61M 2230/205* (2013.01)

(58) Field of Classification Search
CPC .............. A61M 16/204; A61M 16/205; A61M 2016/0021; A61M 2016/0027; A61M 2016/0036; A61M 2016/0039; A61M 2205/15; A61M 2205/3365; A61M 2205/50; A61M 2205/52; A61M 2205/702; A61M 2230/40
USPC ............ 128/204.18, 204.21, 204.23, 204.26, 128/205.25, 848; 600/529, 538
See application file for complete search history.

(56) References Cited

U.S. PATENT DOCUMENTS

| | | | |
|---|---|---|---|
| 5,704,345 | A | 1/1998 | Berthon-Jones |
| 5,820,560 | A | 10/1998 | Sinderby et al. |
| 5,928,189 | A | 7/1999 | Phillips et al. |
| 6,390,091 | B1 | 5/2002 | Banner et al. |
| 6,532,957 | B2 | 3/2003 | Berthon-Jones |
| 6,532,959 | B1 | 3/2003 | Berthon-Jones |
| 6,635,021 | B1 | 10/2003 | Sullivan et al. |
| 6,845,773 | B2 | 1/2005 | Berthon-Jones et al. |
| 6,951,217 | B2 | 10/2005 | Berthon-Jones |
| 7,551,078 | B2 | 6/2009 | Carlson et al. |
| 8,844,525 | B2 | 9/2014 | Schindhelm et al. |
| 2005/0034724 | A1 | 2/2005 | O'Dea |
| 2005/0076615 | A1 | 4/2005 | Wallis |
| 2006/0000475 | A1* | 1/2006 | Matthews ......... A61M 16/0051 128/204.21 |
| 2006/0060190 | A1* | 3/2006 | Sinderby ........... A61M 16/0051 128/200.14 |
| 2006/0102180 | A1 | 5/2006 | Berthon-Jones |
| 2007/0215146 | A1* | 9/2007 | Douglas ................ A61M 16/00 128/200.24 |
| 2007/0293779 | A1 | 12/2007 | Bardy |
| 2008/0004906 | A1 | 1/2008 | Klass et al. |
| 2009/0050154 | A1* | 2/2009 | Strothmann ......... A61M 16/00 128/204.23 |
| 2009/0188499 | A1 | 7/2009 | Chekal et al. |
| 2010/0018530 | A1 | 1/2010 | Schindhelm et al. |
| 2010/0022911 | A1 | 1/2010 | Wariar et al. |
| 2010/0083968 | A1 | 4/2010 | Wondka et al. |
| 2010/0116270 | A1* | 5/2010 | Edwards ............. A61M 16/127 128/201.21 |
| 2010/0180896 | A1 | 7/2010 | Blomquist et al. |
| 2010/0258124 | A1 | 10/2010 | Madaus et al. |
| 2010/0275921 | A1 | 11/2010 | Schindhelm et al. |
| 2011/0000489 | A1 | 1/2011 | Laksov et al. |
| 2011/0263997 | A1 | 10/2011 | Corn |

FOREIGN PATENT DOCUMENTS

| | | |
|---|---|---|
| WO | 96/32055 A1 | 10/1996 |
| WO | 98/52467 A1 | 11/1998 |
| WO | 2004013611 A2 | 2/2004 |
| WO | 2006037184 A1 | 4/2006 |
| WO | 2006066337 A1 | 6/2006 |
| WO | 2007124126 A2 | 11/2007 |
| WO | 2007143535 A2 | 12/2007 |
| WO | 2009026582 A1 | 2/2009 |
| WO | 2009136337 A1 | 11/2009 |
| WO | 2011141916 A1 | 11/2011 |

OTHER PUBLICATIONS

Vasilliou et al. in "Expiratory flow limitation during mechanical ventilation detected by the forced oscillation method", Eur Respir J, 1996, 9, 779-786.
Peslin et al. In "Respiratory mechanics studied by forced oscillations during artificial ventilation", Eur Rospir J, 1993, 6, 772-784.
International Search Report for Application No. PCT/AU2013/000564 dated Aug. 26, 2013.
Dai Yumino and T. Douglas Bradley "Central Sleep Apnea and Cheyne-Stokes Respiration", Proceedings of the American Thoracic Society, vol. 5, No. 2 (2008), pp. 226-236.
White et al., "Role of nocturnal rostral fluid shift in the pathogenesis of obstructive and central sleep apnoea", J Physiol., Mar. 1, 2013, 591, pp. 1179-1193.

* cited by examiner

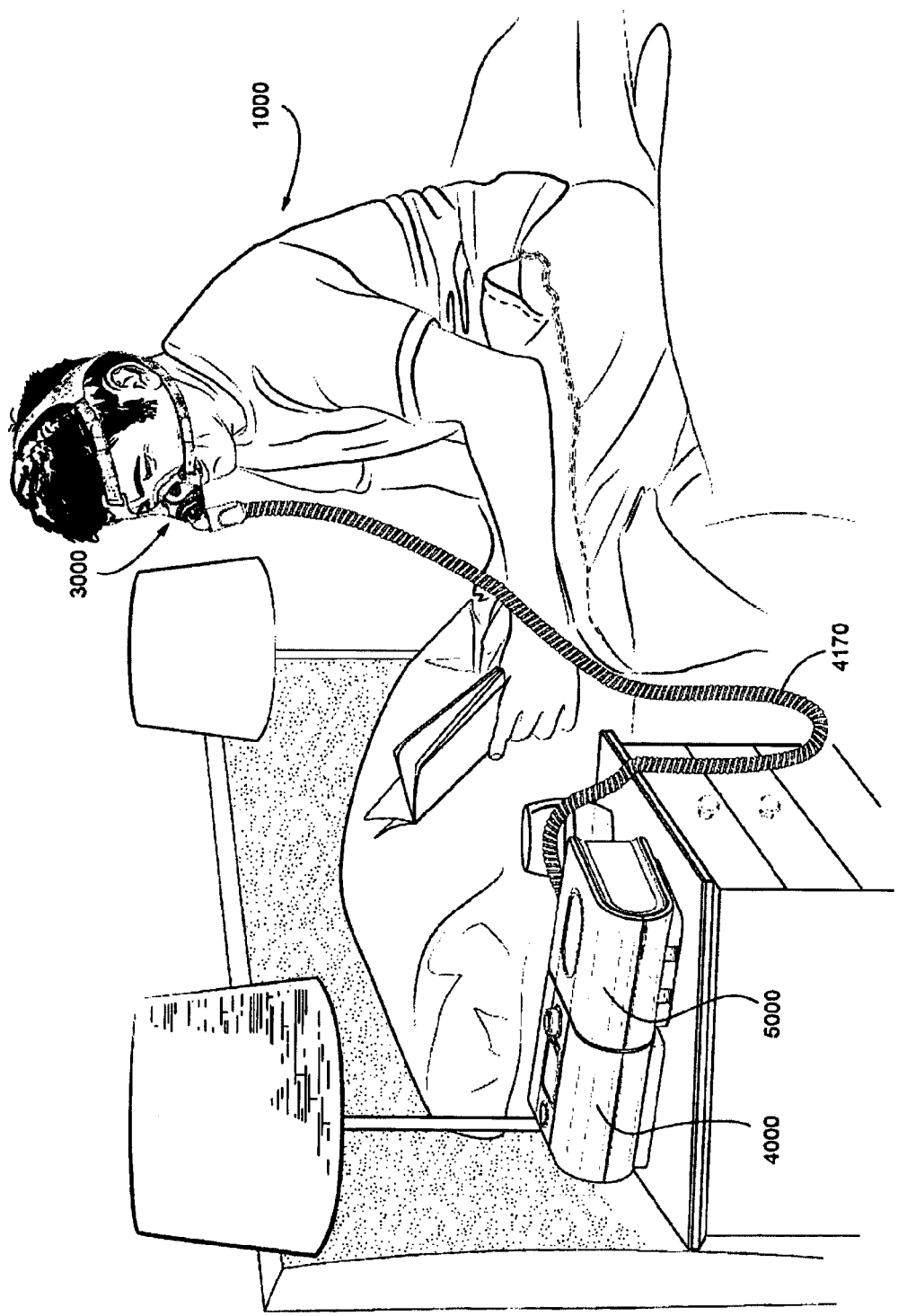

METHODS AND APPARATUS FOR PROVIDING VENTILATION TO A PATIENT

1. CROSS-REFERENCE TO RELATED APPLICATIONS

This patent application claims the benefit of priority to Australian Provisional Patent Applications AU 2011904599 filed 7 Nov. 2011, AU 2012902501 filed 15 Jun. 2012 and AU 2012902693 filed 26 Jun. 2012, the entire contents of each being incorporated herein by reference.

2. BACKGROUND OF THE INVENTION

Field of the Invention

The present technology relates to methods and apparatus for the treatment and/or amelioration of respiratory disorders. In particular, the present technology relates to methods and apparatus for providing ventilation to a patient.

Related Art

The respiratory system of the body facilitates gas exchange. The nose and mouth form the entrance to the airways of a patient.

The airways consist, of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Mechanical ventilators have been used to ameliorate the above respiratory disorders.

3. SUMMARY

The present technology relates to providing ventilation and, in particular, to methods and apparatus for providing ventilation to awake patients.

The present technology also relates to methods and apparatus providing ventilation to sleeping patients.

One aspect of one form of the present technology is a method of providing ventilatory support, or ventilatory assistance, to assist a patient to exercise.

One aspect of one form of the present technology is a ventilator constructed and arranged to assist a patient to exercise.

Another aspect of one form of the present technology is a ventilator constructed and arranged to reduce a ventilatory limitation to exercise as the result of disease.

An aspect of one form of the present technology is a ventilator that is responsive the rate of respiration of a patient.

Another aspect of one form of the present technology relates to methods and apparatus for improving the comfort of awake patients being provided with non-invasive ventilation.

Another aspect of one form of the present technology relates to methods and apparatus for changing ventilation parameters of a ventilator to match patient metabolic demand, in particular when the metabolic demand is changing. In one form the present technology provides an increase to either or both of ventilation and ventilatory support as metabolic load increases.

Another aspect of one form of the present technology is a ventilator that is configurable to move between a plurality of different settings to assist a patient in an exercise regime, as metabolic demand increases, and/or as metabolic demand decreases.

One aspect of one form of the present technology is a processor programmed to implement one or more algorithms.

Another aspect of one form of the present technology relates to a ventilator having a plurality of predefined discrete activity modes or states and moves manually or automatically between modes or states (e.g. (i) Quiet sitting; (ii) Walking around; (iii) Running). In another form, the ventilator has a predefined continuous support pathway, and moves (manually or automatically) along the pathway in response to demand. In this way, an indication of change in metabolic demand and/or lung mechanics is input manually or automatically. Preferably the modes or pathway will have an Expiratory Positive Air Pressure (EPAP) value that ranges from about 4 cmH2O to a limit of about 10 cmH2O. In one form the limit is a predetermined limit. In other forms, the limit is not predetermined and is calculated from a measure of intrinsic PEEP. At this limit, an additional increase, or further increases in demand preferably do not give rise to a further increase in EPAP, hence the level of expiratory positive air pressure will remain substantially constant. Manual adjustments may be made using a remote control, e.g. with buttons and/or joystick.

Another aspect of the present technology relates to apparatus that allows a patient to manually trigger a ventilator to deliver a breath. In particular, the present technology may allow a patient to manually trigger delivery by the ventilator of an inspiration phase of a breath to the patient.

Another aspect of the present technology relates to apparatus that allows a patient to manually cycle a ventilator, and thus to manually cause the device to transition from the inspiratory phase to the exhalation phase. Breaths may be cycled by a mechanical ventilator when a set time has been reached, or when a pre-set flow or percentage of the maximum flow delivered during a breath is reached, depending on the breath type and the settings. Here, preferably breaths can be manually cycled upon a manual cycle command given by a patient.

Another aspect of the present technology relates to apparatus that allows a patient to manually adjust the level of pressure support or the target ventilation of a ventilator.

Another aspect of the present technology relates to apparatus that allows a patient to manually adjust the level of End Expiratory Pressure (EEP) or Expiratory Positive Air Pressure (EPAP) of a ventilator.

Another aspect of one form of the present technology relates to a controller for a ventilator constructed and arranged to calculate a typical duration of a manually triggered breath or a manually cycled breath.

Another aspect of one form of the present technology relates to methods and apparatus that, in a first mode, allow a patient to manually control one or more of the following features; triggering, cycling, the level of pressure support, EEP, or EPAP and the level of target ventilation. In a second mode, the apparatus may provide one or more of automatic triggering, cycling or automatically adjusting the level of pressure support, EEP, or EPAP and the level of target ventilation. In some instances, the automatic adjustments may be based, at least in part, on data obtained from the manual triggering, cycling, target ventilation and/or pressure support level established by the patient.

According to one form of the present technology, a portable battery powered ventilator is provided. In one form the ventilator comprises one or more manual controls constructed and arranged to allow the patient to adjust a ventilator setting between different modes or states, with at least some states being associated with different activity or exercise levels. Alternatively or additionally, the ventilator is constructed and arranged to automatically adjust to different activity or exercise levels of the patient.

In one form of the present technology, a controller for a ventilator is provided, the ventilator being configured to deliver a pressure support waveform to a patient, said pressure support waveform having an inspiratory phase and a subsequent expiratory phase, and the controller being configured to trigger adjustment of at least one parameter of the ventilator in response to indication of a change in metabolic demand and/or lung mechanics of the patient.

In one form, a controller is programmed so that a magnitude of change to the pressure during the expiratory phase is equal to about one third of a magnitude of change during the inspiratory phase.

Preferably the controller is further configured to accept a signal from a metabolic demand responsive transducer, and to determine a state of metabolic demand from said metabolic demand responsive transducer. A metabolic demand responsive transducer may be one or more of an oximeter, a flow sensor and an electromyograph, e.g. a diaphragm electromyograph.

The following further aspects are preferred forms of the present technology.

1. A controller for a ventilator configured to allow a patient to manually, trigger a breath.

2. A controller for a ventilator configured, preferably according to any one of the previous aspects, to allow a patient to manually cycle a breath.

3. A controller for a ventilator, preferably according to any one of the previous aspects, constructed and arranged to calculate a typical duration of a manually triggered breath.

4. A controller for a ventilator, preferably according to any one of the previous aspects, constructed and arranged to calculate a typical duration of a manually cycled breath.

5. A controller for a ventilator, preferably according to any one of the previous aspects, constructed and arranged to automatically trigger to deliver a first breath and to trigger to deliver a subsequent breath after the elapse of a time duration calculated from a duration of at least one manually triggered breath.

6. A controller for a ventilator, preferably according to any one of the previous aspects, constructed and arranged to automatically cycle to stop delivery of a first breath and to cycle to stop delivery of a subsequent breath after the elapse of a time duration calculated from a duration of at least one manually cycled breath.

7. A controller for a ventilator, preferably according to any one of the previous aspects, the controller being configured to allow a patient to manually adjust at least one of the following; a target pressure support, a target ventilation level, IPAP, EPAP, a backup rate, Ti min. and Ti max.

8. A controller, preferably according to any one of the previous aspects, configured to change one of IPAP or EPAP, in response of a change in the other one.

9. The controller of aspect 8, wherein the change in the respective one of the IPAP and EPAP, the change being a response to a change in the other one, is based on a predetermined function.

10. A controller for a ventilator, preferably according to any one of the previous aspects, the controller being configured to; receive signals indicative of level of movement of the patient; and in response to the indicated level of movement, automatically adjust at least one of the following; a target pressure support, a target ventilation level, IPAP, EPAP, a backup rate, Ti min. and Ti max provided to the patient.

11. A controller for a ventilator, preferably according to any one of the previous aspects, the controller being configured to; receive signals indicative of the speed of movement of the patient; and in response to the indicated speed, automatically adjust at least one of the following; a target pressure support, a target ventilation level, IPAP, EPAP, a backup rate, Ti min. and Ti max provided to the patient.

12. A controller for a ventilator, preferably according to any one of the previous aspects, the controller being configured to; receive signals indicative of heart rate of respiration rate of the patient; and in response to the indicated heart rate of respiration rate, automatically adjust at least one of the following; a target pressure support, a target ventilation level, IPAP, EPAP, a backup rate, Ti min. and Ti max provided to the patient.

13. A ventilator comprising the controller of any one of the preceding aspects.

14. The ventilator of aspect 13, the ventilator further comprising a manual controller in communication with the ventilator controller, the manual controller being configured to initiate a manual adjustment of at least one of the following; a target pressure support, a target ventilation level, IPAP, EPAP, a backup rate, Ti min. and Ti max provided to the patient.

15. A ventilator, preferably according to any one of the previous aspects, constructed and arranged to be adaptable to changing patient metabolic demand.

4 BRIEF DESCRIPTION OF FIGURES

FIG. 1 shows apparatus including a push-button, a personal computer and a ventilator in accordance with an aspect of the present technology.

FIGS. 2a and 2b show graphs of pressure (y-axis) provided to a patient, versus time (x-axis) in accordance with an aspect of the present technology and a window in which manual triggering is available. FIG. 2a shows an arbitrary triggering window during an EPAP phase (e.g. an expiratory pressure phase in a pressure waveform provided by a ventilator), in which the patient is free to manually trigger a breath, but in this case, does not manually trigger within the window. In the illustrated form, the window is about 1 second long, although in other forms it may be of a different size. By way of contrast, in FIG. 2b, the patient has initiated early manual triggering.

FIGS. 3a and 3b shows a graph of pressure (y-axis) versus time (x-axis) in accordance with an aspect of the present technology in which manual cycling is available. FIG. 3a shows an arbitrary cycling window during an Inspiratory Positive Airway Pressure (IPAP) phase in which the patient is free to manually cycle the ventilator, but in this case, the patient does not manually cycle the ventilator. In the illustrated form, the window is about 1.8 second long, although in other forms it may be a different size. By way of contrast, in FIG. 3b, the patient has initiated early manual cycling.

Figure 7A:
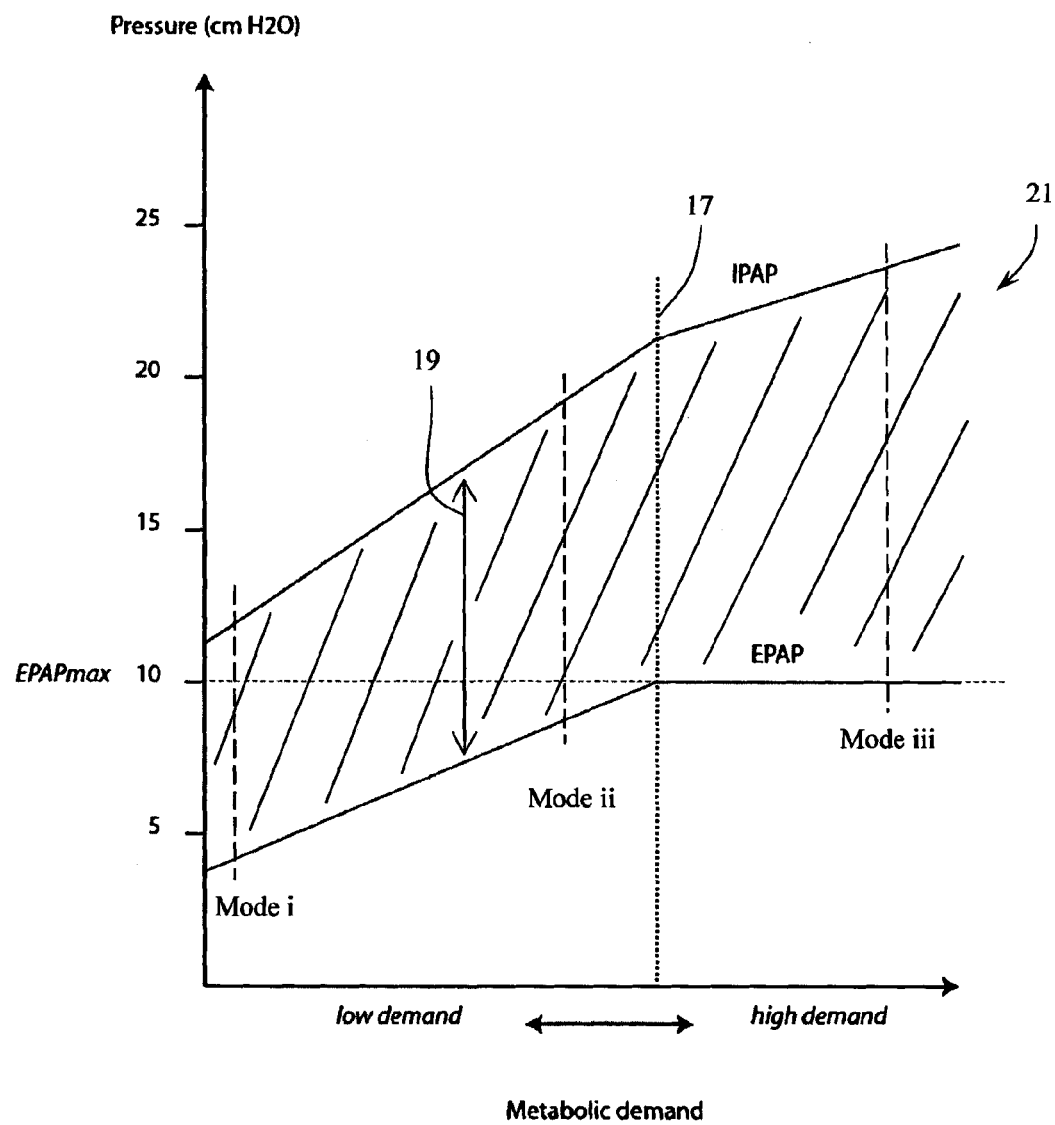
Figure 7B:
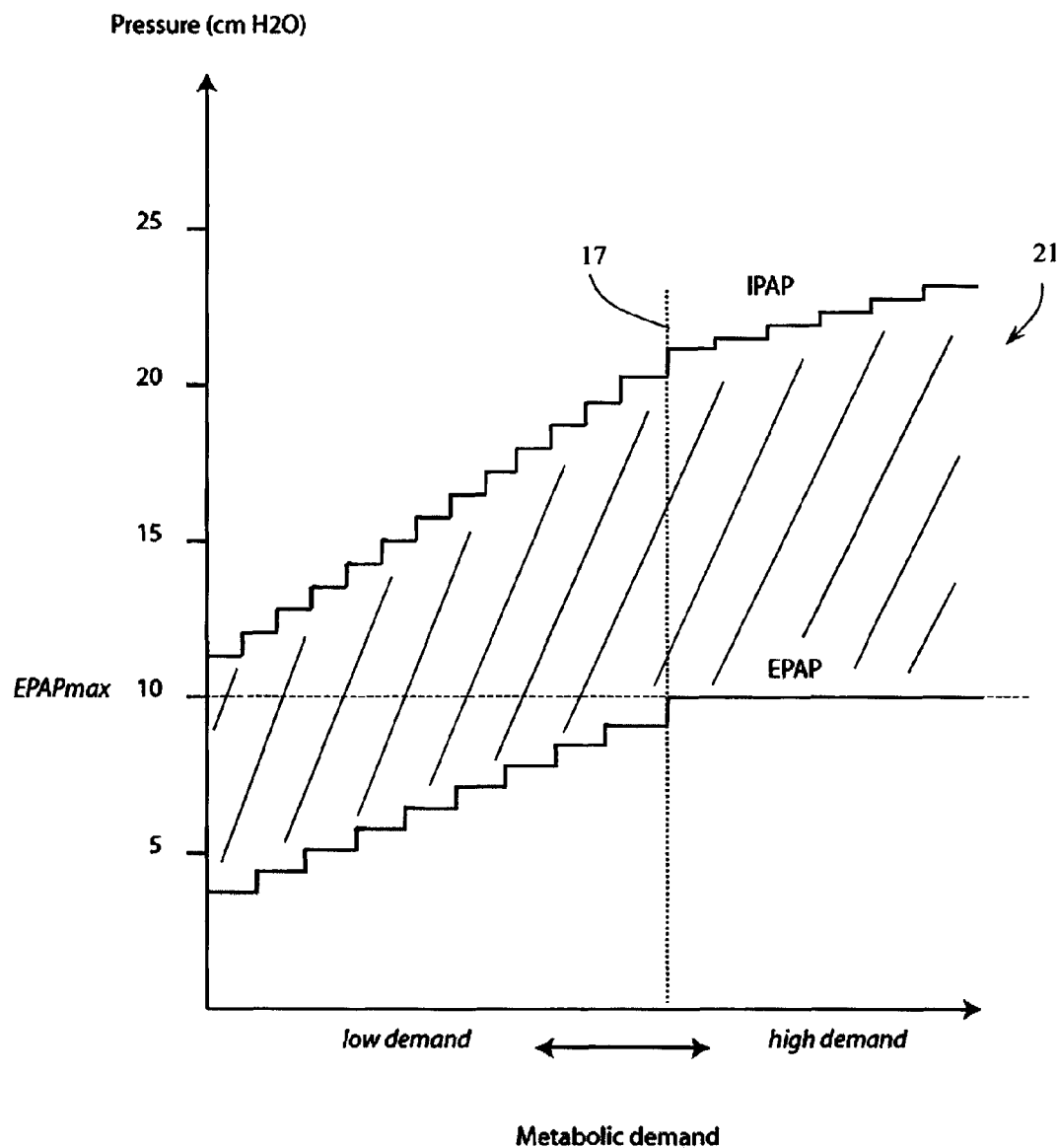

FIGS. 7A and 7B show exemplary options of a pathway in accordance with one aspect of the present technology. The X-axis is metabolic demand, and the Y-axis is pressure. In FIGS. 7A and 7B, two lines are shown, an EPAP line, and an IPAP line. The level of pressure support at a given level of metabolic demand is the difference between the two lines. As the level of metabolic demand increases; both EPAP and IPAP may increase, e.g. at different rates. Hence the level of support may increase from about 7 cmH2O when demand is low, to about 15 cmH2O when demand is high. An EPAPmax limit is defined. As metabolic demand increases, EPAP may increase to a maximum level of EPAPmax, and a further increase in metabolic demand may give rise to a further increase in IPAP, but not to EPAP. The value of EPAPmax may vary from patient to patient. In one form EPAPmax is about 10 cmH2O. In FIG. 7A, the EPAP and IPAP lines are reflective of a continuous change in values in response to changes in demand, however, in an alternative form exemplarily seen in FIG. 7B, there may be discrete changes, hence the lines resemble steps.

Figure 8A:
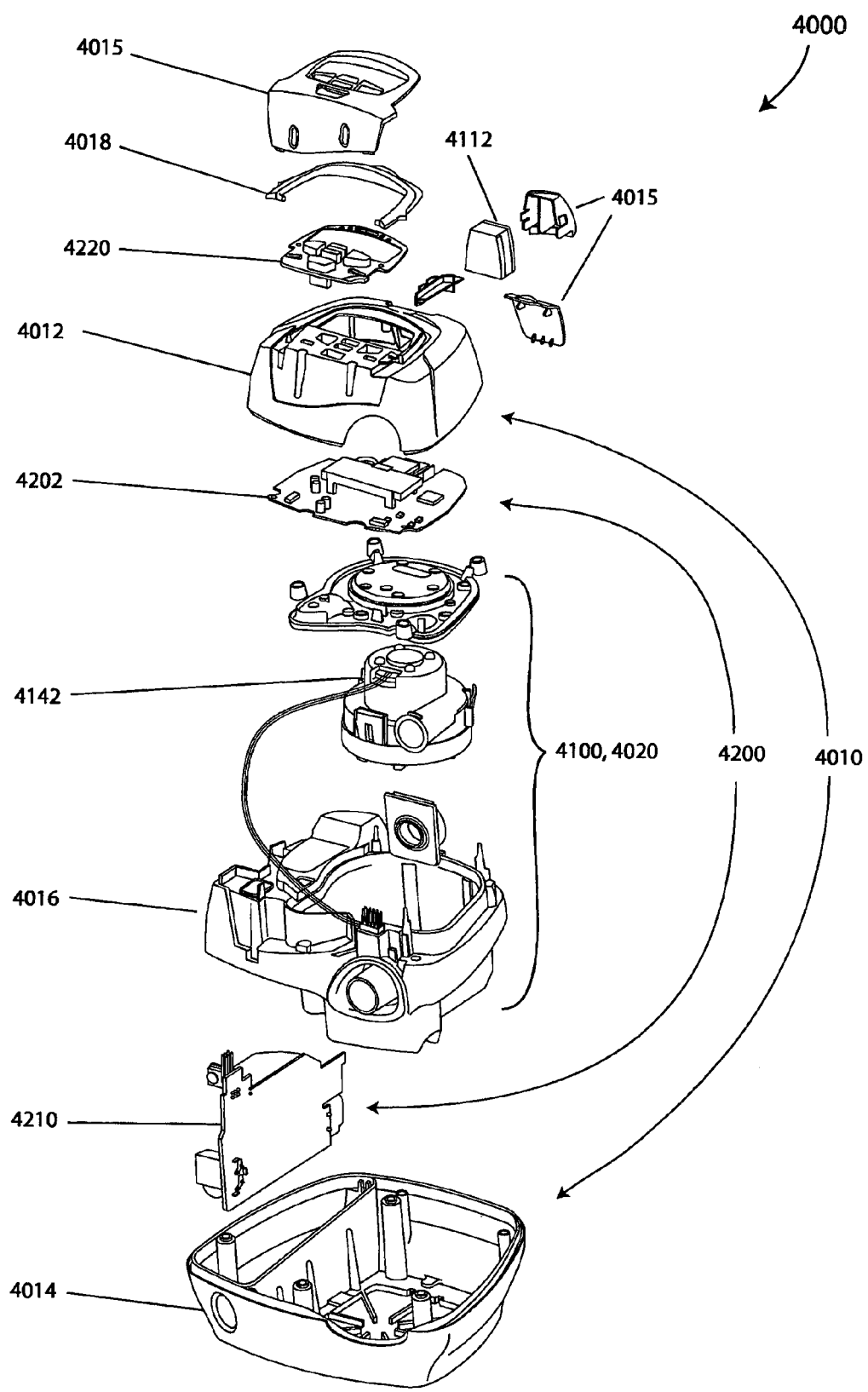

FIG. 8a shows a Positive Airway Pressure (PAP) device in accordance with one form of the present technology.

Figure 8B:
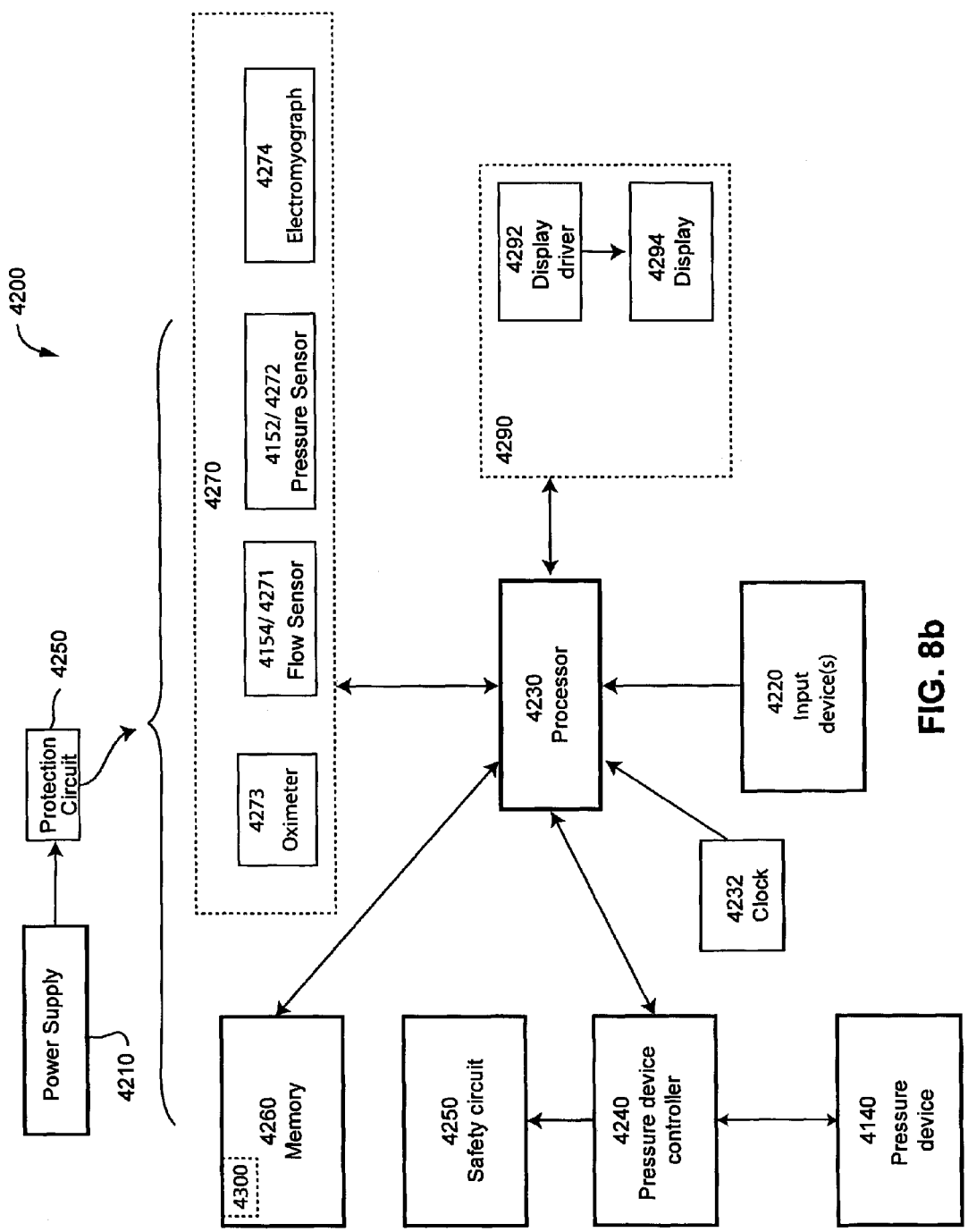

FIG. 8b shows a schematic diagram of electric components for a PAP device in accordance with one form of the present technology.

FIG. 9 shows, in accordance with one form of the present technology, a PAP device connected to a humidifier, providing a supply of air via an air circuit to a patient interface that is being worn by a patient. As depicted, the patient may be sitting quietly reading a book prior to exercising.

Figure 10:
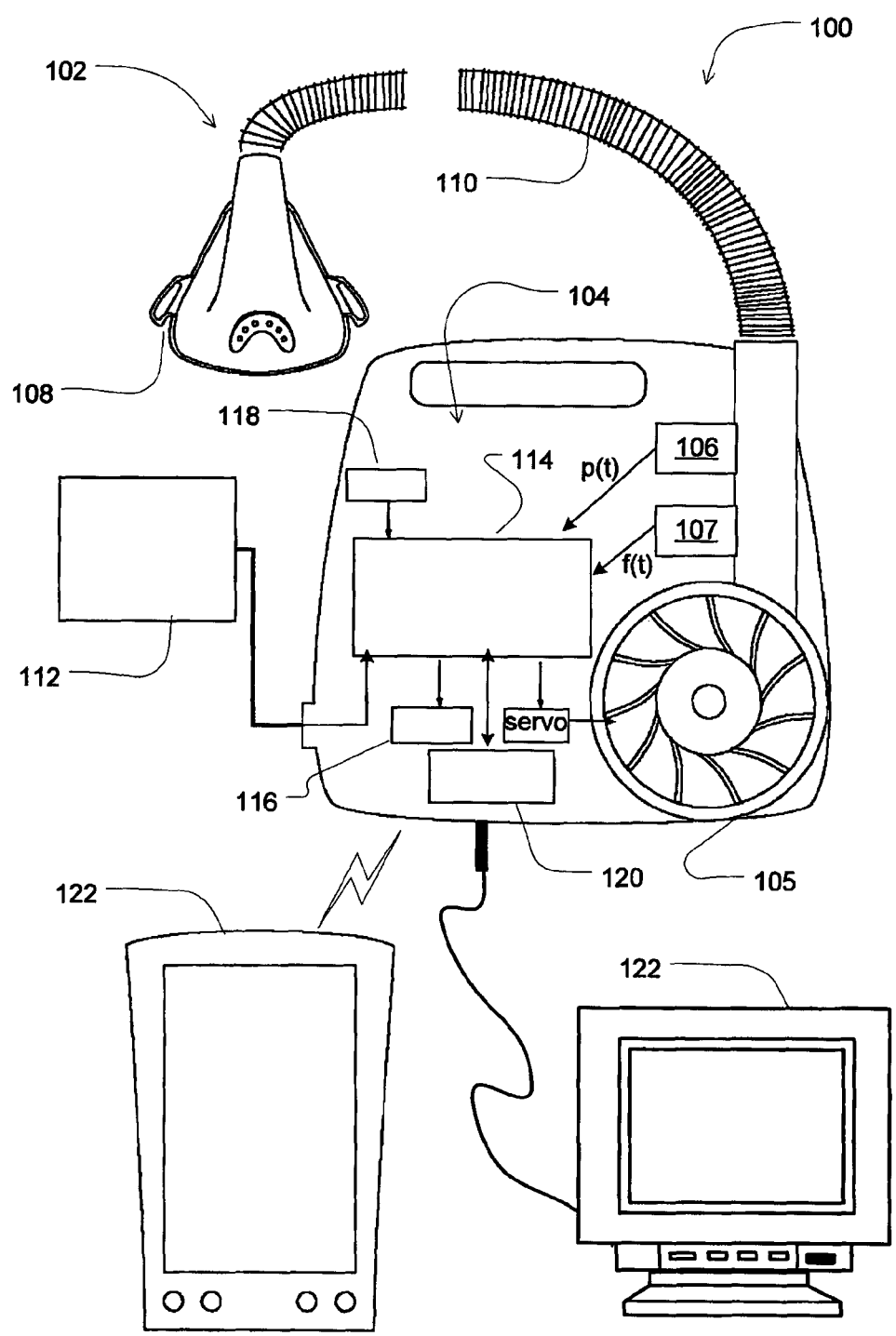

FIG. 10 shows an alternative form of one aspect of the present technology.

Figure 11:
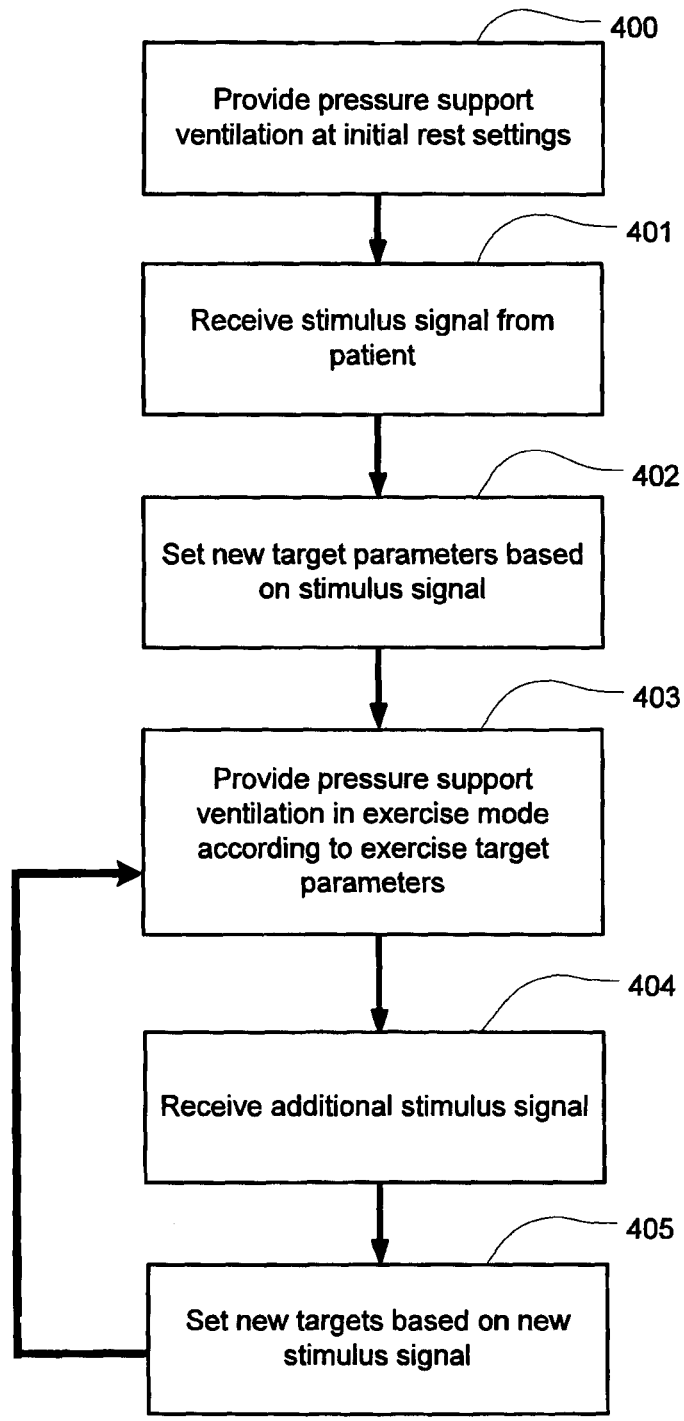

FIG. 11 shows an example flowchart for implementing control of treatment in some aspects of the present technology.

The patient may move the ventilator between different stages or states of demand manually, e.g. by pressing buttons on a remote control. In another form, the ventilator will automatically detect a change in demand e.g. by monitoring one or more of heart rate, breathing (or respiratory) rate, and movement.

5. DETAILED DESCRIPTION

Some patients with certain forms of cardio-respiratory disease, for example COPD or kyphoscoliosis, may benefit from exercise, but find it difficult to exercise. The use of a ventilator may assist the patient to perform exercise, when the ventilator performs at least some of the work of breathing. Should the patient's level of activity change (and corresponding metabolic demand), then a set of ventilator parameters (e.g. level of support, timing of breaths) that might have been appropriate for the first level of activity may be inappropriate for a second level of activity, for example when a patient is becoming more active, or when becoming less active.

Figure 1:
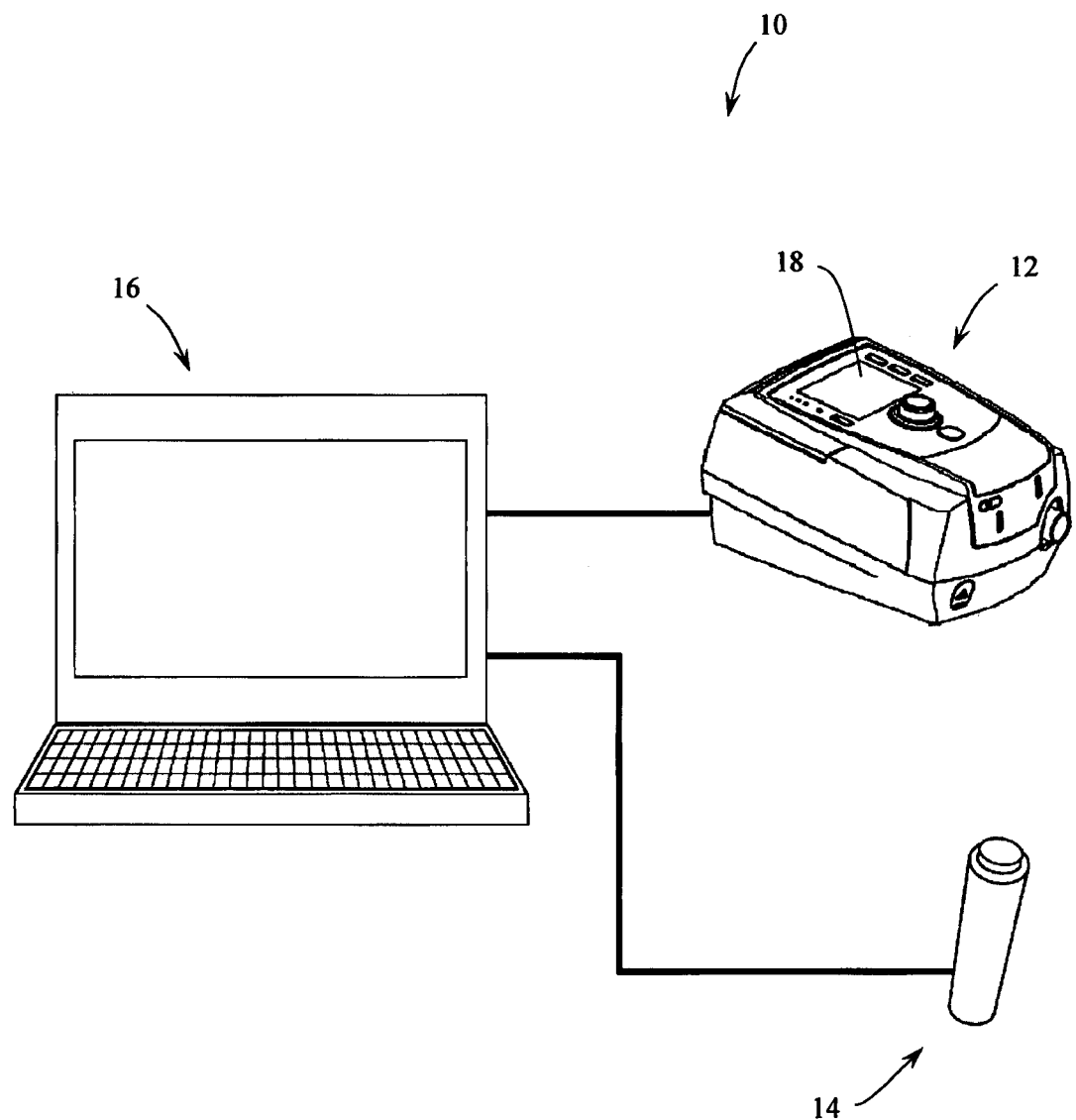

According to one aspect of the present technology, an apparatus 10 is provided as shown in FIG. 1. The apparatus 10 comprises:

A ventilator device 12, for example a Positive Airway Pressure (PAP) ventilator device, further for example a RESMED STELLAR® ventilator;

A user input device or control member, preferably a push-button 14, preferably connectable to other devices such as a personal computer via a Universal Serial Bus (USB); and A controller or a Personal Computer (PC) 16 running a manuals triggering and/or cycling application.

In certain forms of the present technology, the Positive Airway Pressure (PAP) device may be in the form of a device 4000 (see, e.g., FIGS. 8a and 9) that includes an embedded processor 4230 (see, e.g., in FIG. 8b) for executing one or more algorithms that are stored in a memory 4260. This embedded processor 4230 may be provided instead or in addition to the processor existing in the Personal Computer 16 in apparatus 10. In the description hereinbelow where reference is made only to one of the devices 16, 4230 or 12, 4000 it should be understood that same may be applicable also to the other device 16, 4230 or 12, 4000 not mentioned.

5.1 SYSTEMS, ALGORITHMS AND PROCESSES

An aspect of the present technology is one or more algorithms 4300 that may be executed by a controller 16 or a processor 4230. In the accompanying figures algorithm 4300 is indicated in FIG. 8b as being executed by processor 4230; however it is to be understood that algorithm 4300 may also accordingly be executed by controller 16.

5.1.1 Patient Intervention

5.1.1.1 Triggering and Cycling

In this embodiment, the apparatus 10 is programmed and configured so that pressing the button 14 down will trigger the ventilator 12 and releasing the button 14 will cause the ventilator 12 to cycle. The inventors have found that this configuration of push to trigger and release to cycle is easy to use.

In an alternative configuration, there may be different trigger and cycle buttons or different trigger and cycle activators.

In one form, the normal spontaneous triggering and cycling operation is unaffected.

In one form, the successful button-initiated triggering and cycling are subject to certain timing window limits.

In this form, a digital communication interface 18 of the ventilator, preferably a ResMed STELLAR® ventilator, that allows for remote control of settings is used, similar to that used in a sleep laboratory environment. A controller, such as a PC application, monitors the push-button state and sends the appropriate setting changes to the ventilator 12; temporarily changing the parameter "Backup Rate" in the case of triggering and the parameter "TiMax" for cycling.

"Backup Rate", with units of breaths per minute, is a preferred parameter of the ventilator 12 that establishes the minimum number of breaths per minute that the ventilator 12 will deliver, if not otherwise triggered. This parameter may be used to virtually instantaneously trigger a breath. This is so because, if the ventilator 12 is currently in expiration, increasing substantially the Backup Rate reduces the duration of the expiration cycle and effectively triggers a subsequent breath.

"TiMax", with units of time, is a preferred parameter of the ventilator 12 indicative of, the maximum time, from the commencement of a first breath, before the ventilator 12 will automatically change to expiration, if not otherwise cycled. If the ventilator 12 is currently in inspiration, then setting the TiMax to be very short can force a cycle (from inspiration to expiration) in a manner similar to the way an increased backup rate forces a trigger.

A particularity of the ventilator 12 preferably used with this technology, preferably a ResMed STELLAR ventilator, is that the allowable settings of TiMax may be determined by the current setting of Backup Rate.

In the embodiments shown in FIGS. 2a, 2b and FIGS. 3a, 3b; the, preferably STELLAR, ventilator 12 is configured as follows:

For a patient breathing at a nominal 30 breaths per minute (BPM):
Mode: S (i.e. "Spontaneous" mode for detecting a spontaneous breath of a patient)
Backup Rate: 15 BPM
TiMax: 2.0 sec

5.1.1.2 Manual Triggering

The apparatus is further configured so that upon manual activation of the trigger button the apparatus implements the following steps:

(i) Set Backup Rate to 60 BPM (this has the side-effect of changing the TiMax to 0.8 sec)
(ii) Wait 15 ms
(iii) Set Backup Rate back to 15 BPM
(iv) Set TiMax back to 2.0 sec In one form of the present technology, manual triggering of a breath is only possible during an EPAP phase, and/or during a defined portion of the EPAP phase.

However it is noted that in other forms of the present technology, other settings may be used.

5.1.1.3 Manual Cycling

Figure 2A:
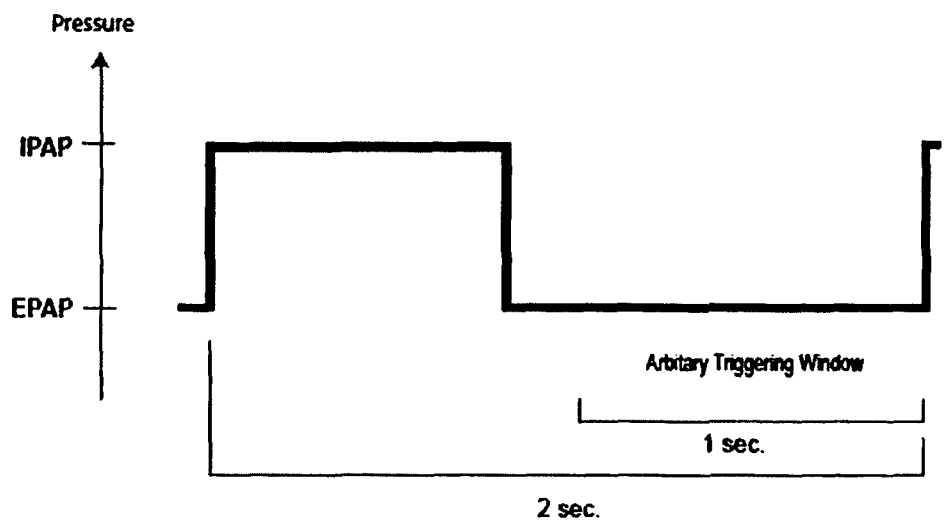
Figure 2B:
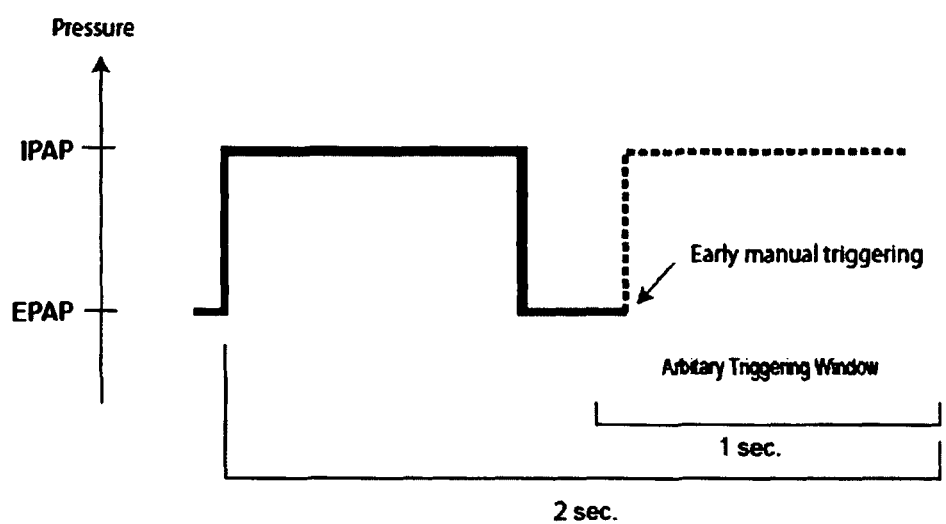

The apparatus is further configured so that upon manual activation of the cycle button the apparatus implements the following steps:

(i) Set Backup Rate to 60 BPM (this allows 0.2<TiMax<0.8)
(ii) Set TiMax to 0.3 sec
(iii) Wait 15 ms
(iv) Set Backup Rate back to 15 BPM
(v) Set TiMax back to 2.0 sec With reference to FIGS. 2a and 2b, the following exemplary scenarios are illustrated. A patient progresses through one or more breaths (one being shown). With the ventilator 12 set to a TiMax of 2 seconds, the next breath will not be delivered until the elapse of 2 seconds. In the illustrated example (see FIG. 2b), the patient manually triggers the ventilator 12 before the elapse of the 2 seconds, and thereupon the next breath will be delivered to the patient. Manually triggering the ventilator may be possible in this example within an "arbitrary triggering window" of 1 second that is indicated in these figures. An exemplary beginning of a next breath that is early manually triggered during this window is indicated in FIG. 2b by a dashed line.

In an embodiment, this is achieved by increasing the backup rate to a rate that is much faster than, a normal rate, for example from 15 BPM to 60 BPM. At this relatively rapid rate, a new breath (indicated accordingly by the dashed line) will be soon delivered. However shortly thereafter, e.g. 15 ms later, the backup rate will be returned to a lower level, e.g. a previous lower level of 15 BPM.

Figure 3A:
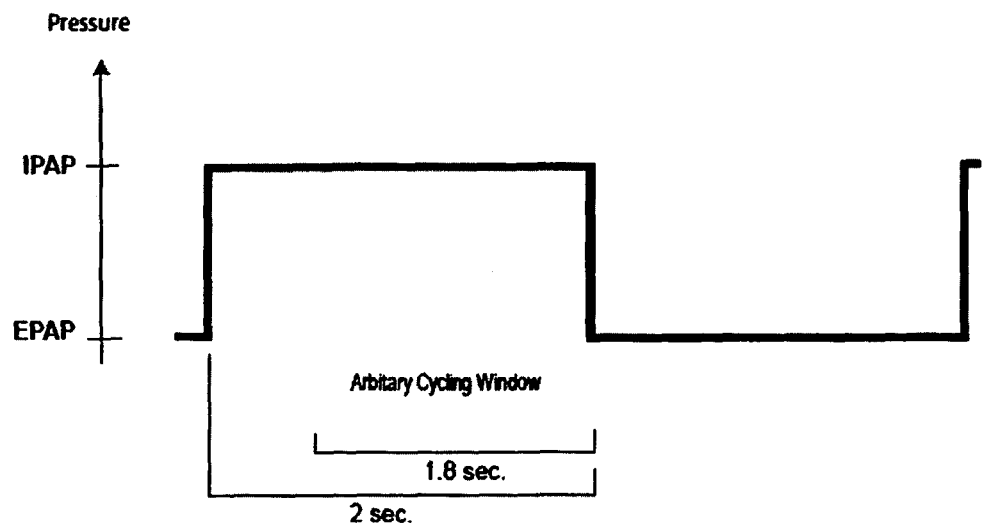
Figure 3B:
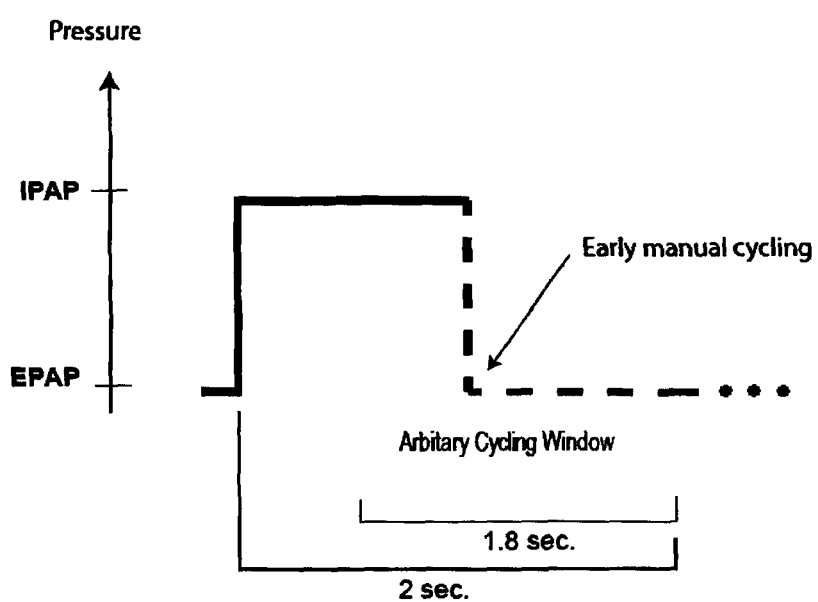

With reference to FIGS. 3a and 3b, in the midst of the ventilator 12 delivering a breath to the patient, the patient activates manual cycling—for example by releasing a button—whereupon the ventilator 12 stops delivering the breath.

In the illustrated embodiment, TiMax is set to e.g. 0.2 sec, a duration that is soon passed, and therefore the ventilator 12 may stop delivering the breath as indicated by the dashed lines in FIG. 3b. Here too there is an "arbitrary cycling window" during the IPAP phase in which the patient is able to manually cycle the ventilator. In these figures, the window is about 1.8 second long.

Other forms of the present technology do not adjust TiMax or Backup Rate, but directly activate triggering and cycling of a ventilator. In one configuration, the ability of the patient for manual intervention may be limited by time constraints.

Figure 4:
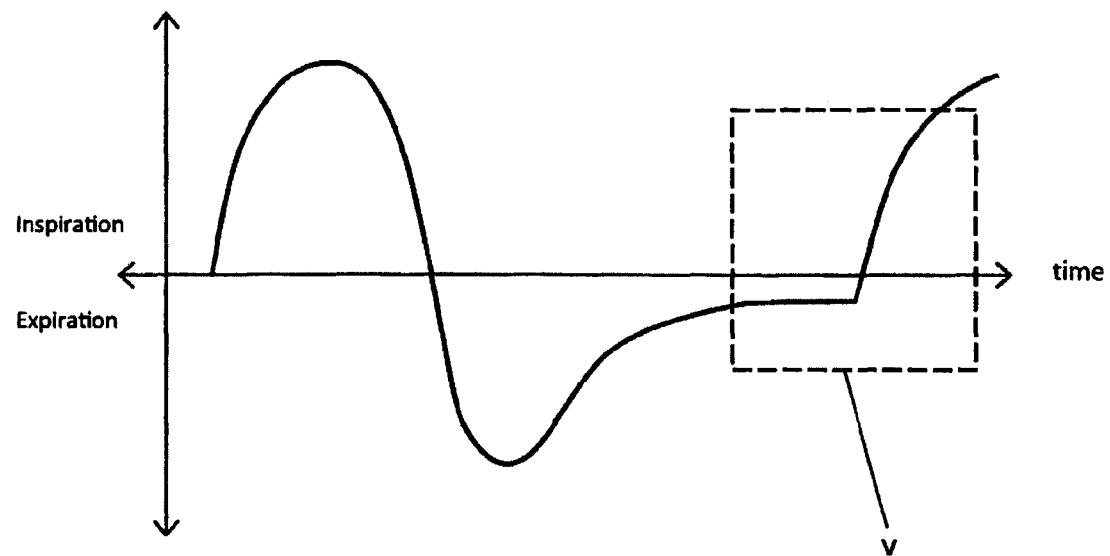
FIG. 4 shows a schematic of flow versus time for a spontaneously breathing patient exhibited through inspiration and expiration cycles of a breathing cycle. A detail of a portion of the breath is shown in FIG. 5.

FIG. 4 shows a schematic of a breath on a flow-time curve, provided by a ventilator that is set to be in "Spontaneous" mode (i.e. S mode). Inspiration is shown as positive flow and expiration as shown as negative flow. This figure shows an example breath with a long exhalation portion.

Figure 5:
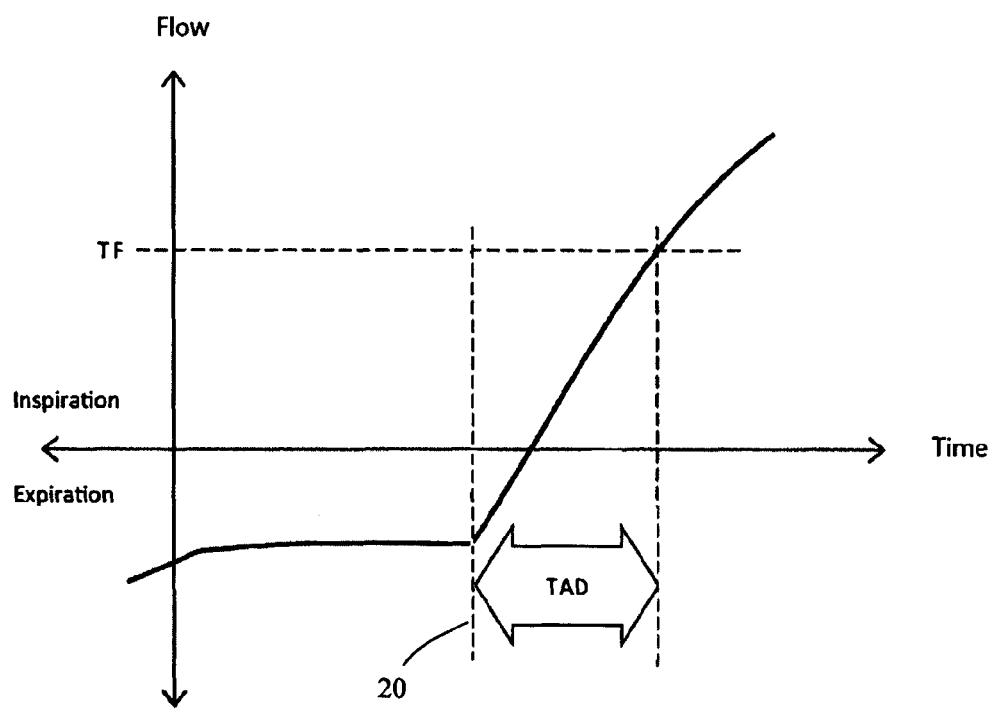
FIG. 5 shows a detail of FIG. 4. In particular, the Figure shows a portion of a breath with two time points, namely the point in time when a button trigger was manually activated ("button trigger") and the time point when the ventilator would have automatically triggered as flow would have exceeded a trigger flow point, ("Standard trigger flow").

FIG. 5 shows a detail from FIG. 4. The Flow axis includes a "trigger flow" threshold TF, and a prior art ventilator may be configured to trigger or provide support to a breath of a patient when measured patient respiratory flow exceeds the "trigger flow" threshold TF. In accordance with the present technology, a supporting breath can be delivered to the patient sooner than would occur in the prior art or in the pre-settings of the ventilator by the patient, e.g., manually, triggering the breath. In FIG. 5, for example, a patient that feels that assistance is needed in order to urge or assist him into inspiration may trigger a supporting breath at an instance indicated by dashed line 20. This may be achieved, as indicated above, by pushing a trigger button. Then, inspiration assistance is provided and inspiration starts. As seen, this will advance the support that a patient may be provided with by a factor of time indicated in this figure as "trigger advance" TAD.

5.1.1.4 Pressure Support and EPAP

In another form of the present technology (not illustrated), the patient manually increases the level of pressure support (e.g. the difference between an IPAP level and an EPAP level) by activation of a button.

In one form of the present technology, not shown, there is a joystick that is used to adjust the level of pressure support. The joystick has a natural neutral position. It may be pushed up, and upon release, it will automatically return to the neutral position. It may also be pushed down, and upon release, it will automatically return to the neutral position.

In one form of the present technology, the apparatus is configured so that once a patient has pushed up and released the joystick, the pressure support will increase by, e.g., 3 cmH2O.

In one form of the present technology, the apparatus is configured so that once a patient has pushed down and released the joystick, the pressure support will decrease by, e.g., 3 cmH2O.

In alternative forms, the amount of change may be different to 3 cmH2O, for example, 1 cmH2O, 2 cmH2O, 4 cmH2O, 5 cmH2O, or some other amount.

Alternatively, moving the joystick may continuously change the provided pressure support. The patient can then decide to lock the instantaneous pressure support achieved at a particular point, or let it automatically return to its initial level. The rate of change of the pressure support, whether driven by the patient or during the automatic return to a predefined rate, may also be predetermined, manually adjustable or both.

For example, in a ventilator delivering a pressure waveform having two levels, namely an inspiratory pressure (IPAP) and an expiratory pressure (PEEP or EPAP), the patient may be able to manually adjust one or both of IPAP and PEEP or EPAP.

In an, alternate, regardless of whichever of the IPAP and EPAP are adjusted, the other may also change. The change may be associated with a predetermined function. Thus, in response to the patient's manual control inputs, the IPAP and EPAP will change together, according to this predetermined function relating the change in EPAP with the change in the IPAP.

In one form, the IPAP and EPAP may be approximately related by the function:

$$\Delta(IPAP)=3\times\Delta(EPAP),$$

i.e., the patient increasing the IPAP by 3 cmH2O will automatically increase the EPAP by 1 cmH2O.

It has to also be appreciated that in some instances, instead of changing the pressure support, IPAP or EPAP, a patient may manually (or the ventilator automatically) adjust a respective target ventilation level.

Also, whilst any one of a number of ventilation parameters may be individually adjustable by the patient, it is envisaged that similar functionality may be better facilitated by offering various modes of operation of the ventilator, each mode having specific set of ventilation parameters. For example, instead of being offered a large number of separate parameters for manual adjustment, a patient may be offered three different modes: "resting", "gentle exercise" and "moderate exercise". Each of these modes or states may be associated with a specific set of ventilation parameters, such as respiratory rate, pressure support, target ventilation level, EEP, EPAP etc.

In one form, the patient may manually adjust the pressure waveform provided by the ventilator, by selecting between running values (i.e. non-discrete) or discrete values of metabolic demand appropriate e.g. to the level of activity or work he is experiencing. Selecting a certain metabolic demand accordingly sets a corresponding location along the pathway 21, and together with that a level of EPAP; IPAP and pressure support. Manual selection of the metabolic demand may be performed by e.g. pressing buttons on a remote control.

5.1.1.5 Tidal Volume

In one form, the ventilator comprises a control that allows a patient to adjust a tidal volume setting of the ventilator.

5.1.1.6 Oxygen

In one form of the present technology, oxygen is delivered to the patient. In accordance with one form of present technology, a patient may manually increase or decrease the flow rate of oxygen.

5.1.1.7 Humidification

In one form of the present technology, the patient can adjust a level of humidification provided by the ventilator 12 or 4000 by a humidifier 5000 (see e.g. FIG. 9 where device 4000 is shown with humidifier 5000). For example the patient may be able to increase or decrease a level of relative and/or absolute humidity.

5.1.1.8 Temperature

In one form, the patient can adjust a temperature of air delivered.

5.1.1.9 Waveform

In one form of the present technology, the patient can adjust the shape of the pressure waveform. For example, the patient may be able to vary the pressure waveform from a more square wave to a more rounded or smoother waveform. In alternative arrangement, the patient may be able to select a waveform from a set of predefined waveforms.

5.1.2 Cruise Control

In another form of the present technology, the apparatus 10 is programmed and configured to operate in a semi-automatic fashion, e.g. to learn a pattern of manually activated triggers, and/or cycles. The ventilator is able to learn from the patient a setting appropriate to the current level of activity. In one form a processor, e.g. 4230, is programmed to execute one or more algorithms as follows. For example, the patient may manually trigger the ventilator 12 or 4000 a number of times over several breaths. The apparatus 10 calculates a patient preferred period between breaths and then upon activation of a "CRUISE CONTROL" mode, delivers breaths at the patient preferred rate.

In one form, the apparatus 10 is programmed and configured, to determine a running average duration between manually triggered breaths. In one form the apparatus 10 determines a running average duration between manually cycled breaths.

In one form, the apparatus 10 is programmed and configured to store a time, t0, when the manual trigger is first pressed, and also to store the times, t1, t2, t3 when a new trigger and subsequent triggers are pressed. For example, the times may be stored in an array of time values t(i), having an array index i by which time values, where i is an integer, e.g. so that some consecutive time values of t(i) may be found. The differences t1−t0, t2−t1 and t3−t2 are calculated and an average is taken and stored.

In one form, the apparatus 10 is programmed and configured to store a time, c0, when a manual cycle is first activated (e.g. by release of a button), and also to store the times, c1, c2, c3 when subsequent cycles are activated. The differences c1−c0, c2−c1 and c3−c2 are calculated and an average is taken and stored.

Figure 6:
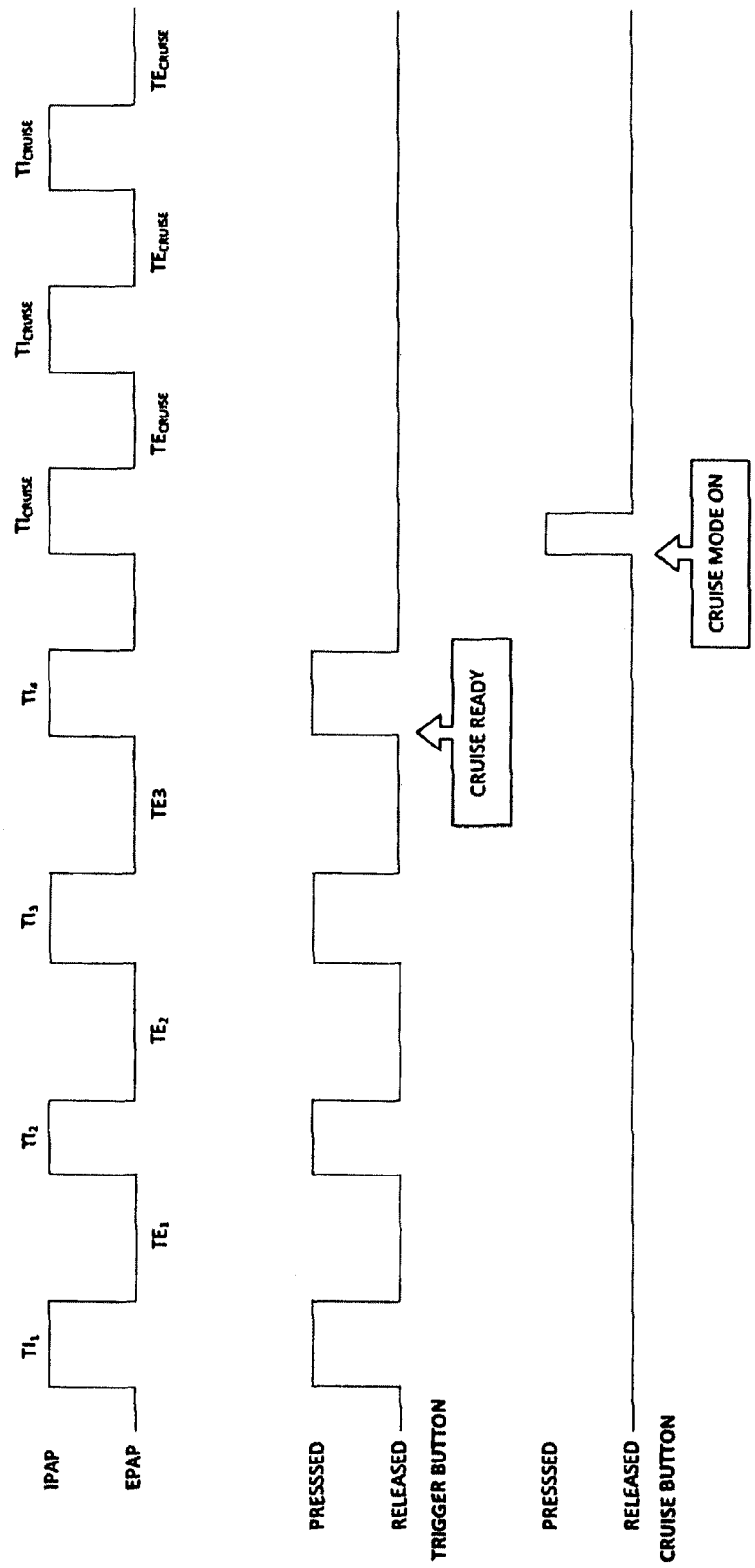
FIG. 6 illustrates over time pressure, and activation status of a trigger button and a cruise-control button.

FIG. 6 illustrates three lines: a pressure waveform delivered by a ventilator (top), trigger button signal (middle) and cruise button signal (bottom). When the trigger button is pressed, the ventilator triggers to deliver a breath at a pressure of IPAP, and when it is released, the ventilator cycles to deliver a breath at a pressure of EPAP. The duration of the first inhalation portion of the breathing cycle is TI1. The duration of the second and third inhalation portions are TI2 and TI3, respectively. The durations of the first, second and third exhalation portions are TE1, TE2 and TE3 respectively.

In one form of the present technology, the apparatus 10 calculates TEcruise, as the average of the last three inhalations, e.g. TI1, TI2 and TI3; and furthermore preferably the apparatus 10 calculates TEcruise, as the average of the last three exhalations, e.g. TE1, TE2 and TE3. Preferably the average is calculated as a running average, so that if the patient continues to manually trigger and cycle, the average times will be updated. In one form, the average may be calculated from last "k" recent stored time values of t(i), with "k" being an integer not exceeding "m", where "m" is a integer between "0" and "n", the number of samples.

Upon activation of the "CRUISE CONTROL" mode by pressing e.g. the "cruise" button, the ventilator 12 will trigger and subsequently cycle at the average cycle time calculated in the averaging step. See FIG. 6, "Cruise Mode On".

For example, as shown in FIG. 6, when Cruise control is activated, the last three inhalations are TI4, TI3 and TI2, and the last three exhalations are TE3, TE2, and TE1.

Hence

TIcruise=(TI4+TI3+TI2)/3

TEcruise=(TE3+TE2+TE1)/3

In one form of the present technology, output devices 4290 e.g. feedback lights and/or chimes are included (see FIG. 8*b*). When the apparatus 10 has sufficient data a light and/or chime at e.g. the ventilator 12 or 4000 will be activated to indicate that the ventilator 12 or 4000 is ready to go into cruise control mode. See FIG. 6 "Cruise Ready".

In this way, a patient can adjust a breath length from that which would be delivered but for the patient intervention.

In one form of the present technology, a warning light and/or chime will be activated if the patient attempts to enter cruise control mode when the apparatus 10 is not ready to enter cruise control mode.

In one form of the present technology, an indicator light and/or chime will be activated if the patient successfully enables cruise control mode, and remains activated while cruise control mode is in effect.

5.1.3 Response to Changing Metabolic Demand or Lung Mechanics

Another aspect of one form of the present technology is a device that is constructed and arranged to be able to provide automatically a suitable pressure waveform in response to changing metabolic demand.

Methods and apparatus are provided to determine a suitable pressure waveform, including the steps of adjusting the level of EPAP, and/or IPAP, and/or pressure support provided to the patient, with pressure support being the difference between EPAP and IPAP.

In another form, providing a sufficient pressure waveform can be performed by following, e.g. at the controller 16, 4230 or ventilator 12, 4000, a predefined continuous support pathway for determining the required pressure waveform for the patient. An example of such a continuous pathway can be seen indicated as 21 in FIG. 7A. Here, the pathway 21 is illustrated by the hatched area and is defined by an EPAP line and an IPAP line, that respectively bound the pathway from below and above.

According to the pathway 21 of FIG. 7A, as the level of metabolic demand increases, e.g. within a first, range of metabolic demand values, the levels of IPAP and EPAP increase together, for example increasing linearly, with it until an inflection point, here indicated by 'dotted line' 17, is reached. As the level of metabolic demand increases beyond this line 17, the level of IPAP also increases, preferably however here at a different rate, optionally lower than before. The EPAP level as seen may be maintained after this point at a constant level, here defined as EPAPmax, which in one form is about 10 cmH2O. The level of pressure support in the pathway is accordingly defined for each given value of metabolic demand as the difference between IPAP and EPAP for that given value. Here, the pressure support at a certain value of metabolic demand is indicated by 'double sided arrow' 19.

As seen in FIG. 7B, changes in the level of pressure support may also vary discretely with change in metabolic demand. Here, these discrete changes are obtained by the IPAP and EPAP lines being stepped shaped. The optional lower rate of increase in IPAP level after the inflection point indicated by line 17; is achieved in this pathway by smaller steps of increase in the IPAP level.

In yet another form, pre-defined discrete levels of work or metabolic demand of a patient may be defined, and the apparatus 10 or ventilator 12, 4000 may be configured to enable automatic selection of (or movement between) these discrete levels. Such pre-defined levels may be defined as: (i) Quiet sitting (e.g. when the body is at rest); (ii) Walking around (e.g. when the body is at normal average activity); (iii) Running (e.g. when the body is at a high level of activity). And, the level of e.g. pressure support at each mode can be: (i) Quiet sitting—about 7 cmH2O to about 9 cmH2O, more preferably about 7 cmH2O; at mode (ii) Walking around—about 10 cmH2O to about 13 cmH2O, more preferably about 11 cmH2O; and at mode (iii) Running—about 14 cmH2O to about 17 cmH2O, more preferably about 15 cmH2O.

Optionally, a form of apparatus 10 may be configured to function with such discrete levels of metabolic demand and in addition with the pathway 21. Thus, the dashed lines seen in FIG. 7A indicate the modes (i), (ii) and (iii) of such a form of apparatus 10, and as seen selecting a mode may affect in this form also the level of EPAP and IPAP that is provided to the patient. For example, moving from mode (i) to (ii) may also increase the levels of EPAP and IPAP in addition to pressure support.

5.1.4 Rate Responsive Ventilator

In one form, the pressure waveform provided by the ventilator may be automatically set by detecting changes in metabolic demand e.g. by monitoring one or more of heart rate, breathing (or respiratory) rate, and movement, or state of movement. In one form of the present technology a sensor configured to provide a measure of metabolic demand, e.g. heart rate and breathing (or respiratory) rates, provides an input to a processor. In one form the metabolic demand responsive sensor is an oximeter 4273 used to detect heart rate and/or respiratory rates (see, e.g., oximeter 4273 indicated in FIG. 8*b*).

In one form an oximeter 4273 is used to provide a photoplethysmogram (PPG). One or more respiratory parameters are extracted from a PPG signal using a time-domain, and/or a frequency-domain processing step. For example, wavelet-based analysis may be used.

In one form a value for heart rate variability is determined from a signal from an oximeter 4273. The value of heart rate variability is used to estimate a level of activity of the vagal nerve, and to infer a measure of metabolic demand.

In one form, in a further processing step, a respiratory parameter extracted from a PPG signal is used, preferably in conjunction with a parameter extracted from a flow sensor, to estimate a respiratory rate, or as an input to a respiratory rate state machine.

A control algorithm monitors the respiratory rate and in response to a change of respiratory rate, or a change in state of a respiratory rate state machine, adjusts one or more of IPAP and EPAP.

In one example, when the estimated respiratory rate increases, the ventilator or PAP device increases the IPAP level. In a further example, when the estimated respiratory rate increases, the ventilator or PAP device increases the EPAP level.

In one example, when the estimated respiratory rate decreases, the ventilator or PAP device decreases the IPAP level. In a yet further example, when the estimated respiratory rate decreases, the ventilator or PAP device decreases the EPAP level.

In this way the ventilator is able to respond automatically to the respiratory rate of the patient, and to assist the patient to exercise.

In one form, actigraphy, e.g. accelerometers, are used to detect movement of the patient. When a patient starts to walk or exercise, the level of movement of the patient is detected and used to respectively increase at least one of a respiratory rate (e.g. breaths per minute), and/or level of pressure support and/or target ventilation.

In one form, an exercise machine is connected to the ventilator. When a patient begins to exercise, the movement of the machine provides an input to the ventilator to alter a rate and or a level of pressure support or target ventilation.

In one form, a wearable sensor is used to detect movement of the patient and as an input to control the ventilator. For example, a Global Positioning Sensor (GPS) may be used to detect a movement of the patient. The change in location and the corresponding differences in time may indicate the speed of the patient. The measured speed can be used as an indication of whether and how quickly the patient is moving. Such an indication may then be used to trigger a corresponding change in the ventilation parameters, such as provided respiratory rate, level of pressure support or target ventilation level. In one configuration, the system may include a lookup table which relates a specific speed with a specific respiratory rate, pressure support or target ventilation level. A maximum speed limit, i.e. higher than 1 m/s, may be imposed and speeds higher than the speed limit may be ignored, as they may be indicative of the patient movement being assisted by a third party or by transportation means.

In one form, an analogue sensor or controller is used that is configured to provide a greater level of support the harder it is pressed. In another form, an analogue sensor or controller is used to trigger and/or cycle the ventilator.

5.1.5 Determining EPAP

In one form of the present technology, expiratory pressure level (EPAP) is set automatically to a level at or slightly below the intrinsic positive end expiratory pressure (PEEP), e.g. as determined by reducing or minimising Expiratory Flow Limitation (EFL). The presence of EFL may be determined using a forced oscillation technique.

In one form the presence of EFL is determined using a technique such as that described in Peslin et al. (1993) EUR RESPIR J, 6, 772-784, "Respiratory mechanics studied by forced oscillations during artificial ventilation".

In one form the presence of EFL is determined by applying a sinusoidal pressure waveform, e.g. at 5 Hz, 10 Hz and 20 Hz at the entrance to the airways, e.g. using a loudspeaker placed in parallel with the ventilator, or by applying an oscillatory pressure waveform signal to a blower under the control of a processor. The airway is modelled as a combination of resistance, compliance and in one form, inertance. Complex impedances in inspiration and expiration are determined. Intrinsic PEEP is determined by adjusting EPAP and finding the lowest value of EPAP which reduces the magnitude of the difference between the inspiratory and expiratory values of the imaginary component of complex impedance to a level close to that seen in normal patients, or finding the lowest value of EPAP above which a further increase no longer yields a significant decrease in this difference.

This step of determining an EPAP level using a forced oscillation technique may, be combined with a step of determining a respiratory rate from an oximeter 4273 and/or a flow sensor.

5.1.6 Patient Responsive Algorithm

In one form of the present technology, the processor e.g. 4230 is configured to execute an algorithm that includes the following steps:

(i) Adjust tidal volume and respiratory rate to maintain minute ventilation at a value between a predetermined minimum minute ventilation and a predetermined maximum minute ventilation;

(ii) Receive a patient initiated synchrony stimulus;

(iii) Determine a minimum target respiratory rate on the basis of a patient initiated synchrony stimulus; and (iv) Adjust respiratory rate in response to the patient initiated synchrony stimulus.

5.2 APPARATUS/DEVICE

In one form of the present technology, a ventilator 12 takes the form of PAP device 4000.

PAP device 4000 comprises mechanical and pneumatic components 4100, electrical components 4200 and is programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, and a pressure device 4140 such as a controllable source of air at positive pressure (preferably a blower 4142). One or more pressure sensors 4152 and flow sensors 4154 are included in the pneumatic path.

The preferred pneumatic block 4020 comprises a portion of the pneumatic path that is located within the external housing 4010.

The PAP device 4000 preferably has an electrical power supply 4210, one or more input devices 4220, a processor 4230, a pressure device controller 4240, one or more protection safety circuits 4250, memory 4260, transducers 4270 and one or more output devices 4290. Electrical components 4200 may be mounted on a single Printed Circuit Board Assembly (PCBA) 4202. In an alternative form, the PAP device 4000 may include more than one PCBA 4202. See, e.g., a component 4200 and a PCBA 4202 indicated in FIG. 8a.

The PAP device 4000 is connected to a patient 1000 via an air circuit 4170 in use, e.g., as indicated in FIG. 9.

5.2.1 Electrical Components 5.2.1.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and a humidifier 5000.

In one form of the present technology power supply 4210 is a battery. Preferably the battery has at least enough energy to power the PAP device 4000 to allow a patient to exercise for a period, e.g. about 1 to about 2 hours, alternatively the period is about 2 hours to about 4 hours.

5.2.1.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a processor 4230.

In one form the input device 4220 may be constructed and arranged to allow a person to select a value and/or a menu option.

5.2.1.3 Processor 4230

In one form of the present technology, a processor 4230 suitable to control a PAP device 4000 is an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal (s) from one or more transducers 4270, and one or more input devices 4220.

The processor 4230 is configured to provide output signal (s) to one or more of an output device 4290, and a pressure device controller 4240.

The processor 4230 is configured to implement the one or more algorithms expressed as computer programs stored in memory 4260.

5.2.1.3.1 Clock 4232

Preferably PAP device 4000 includes a clock 4232 that is connected to processor 4230.

5.2.1.4 Pressure Device Controller 4240

In one form of the present technology, pressure device controller 4240 is located within processor 4230.

In one form of the present technology, pressure device controller 4240 is a dedicated motor control integrated circuit. For example, in one form a MC33035 brushless DC motor controller, manufactured by ONSEMI is used.

5.2.1.5 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

5.2.1.6 Memory 4260

In accordance with one form of the present technology the PAP device 4000 includes memory 4260, preferably non-volatile memory. One or more of the algorithms described above are stored in memory 4260 and executed by processor 4230 in use.

In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

5.2.1.7 Transducers 4270

Transducers may be internal of the device, or external of the PAP device. External transducers may be located for example on or form part of the air delivery circuit, e.g. the patient interface. External transducers may be in the form of non contact sensors that transmit or transfer data to the PAP device.

5.2.1.7.1 Flow 4271

A flow transducer 4271 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal from the flow transducer 4271, is received by the processor 4230.

5.2.1.7.2 Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor 4230. In one form, the signal from the pressure transducer 4272 is filtered prior to being received by the processor 4230.

Processor 4230 uses a signal from the pressure transducer 4272 to assist in control of the pressure delivered to the patient 1000 via patient interface 3000.

5.2.1.7.3 Oximeter 4273

An oximeter 4273 in accordance with the present technology may be an oximeter from one of the following manufacturers: PHILIPS, MASIMO, NELLCOR. For example, a NELLCOR OxiMax sensor may be used.

5.2.1.7.4 Electromyograph 4274

In one form of the present technology an electromyograph (EMG) 4274 is provided. The EMG 4274 is configured to monitor activity of the diaphragm of the patient.

5.2.1.8 Output Devices 4290

An output device 4290 in accordance with the present technology may take the form of one or more of a visual, audio and haptic unit. A visual display 4294 may be a Liquid Crystal Display (LCD) or Light Emitting Diode (LED) display, and a display driver 4292 may be used for displaying information on the display 4294.

5.3 ADDITIONAL OR ALTERNATIVE ASPECTS

An example form of a device for implementing one or more of the methods of the present technology is illustrated in FIG. 10. In some forms, the apparatus 100 may include a patient respiratory interface 102, a delivery tube 110, a controller 104 and a flow generator such as a servo-controlled blower 105.

The patient respiratory interface such as a mask 108 as shown together with the delivery tube 110, provides a respiratory treatment to the patient's respiratory system via the patient's mouth and/or the patient's nares. Optionally, the patient respiratory interface may be implemented with a nasal mask, nose & mouth mask, full-face mask or nasal pillows or tracheostomy tube.

With the flow generator, the apparatus 100 can be configured to generate a respiratory pressure treatment at the patient respiratory interface. To assist this end, the device may further include a pressure sensor 106, such as a pressure transducer to measure the pressure generated by the blower 105 and generate a pressure signal p(t) indicative of the measurements of pressure. In such a device, the delivery tube 110 may serve as the sense tube to permit detection of pressure levels supplied to the mask or patient respiratory interface.

The apparatus 100 may also optionally be equipped with a flow sensor 107, which may be coupled with the patient respiratory interface. The flow sensor generates a signal representative of the patient's respiratory flow. The signals from the sensors may be used to detect obstructive or central apneas, hypopneas, cardiogenic airflow, respiratory rates and other respiratory related parameters from the signals measured by the sensors as discussed in more detail herein. In some forms, flow proximate to the mask 108 or delivery tube 110 may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. Although the pressure or flow sensors are illustrated in a housing of the controller 104, they may optionally be located closer to the patient, such as in the mask 108 or delivery tube 110. Other devices for generating a respiratory flow signal or pressure signal may also be implemented. For example, a motor RPM sensor may be utilized to estimate pressure or flow information supplied by the flow generator device based upon the characteristics of the system.

Based on flow f(t) and/or pressure p(t) signals, the controller 104 with one or more processors 114 generates blower control signals. For example, the controller may generate a desired pressure set point and servo-control the blower to meet the set point by comparing the set point with the measured condition of the pressure sensor. Thus, the controller 104 may make controlled changes to the pressure delivered to the patient interface by the blower. Optionally, such changes to pressure may be implemented by controlling an exhaust with a mechanical release valve (not shown) to increase or decrease the exhaust while maintaining a relatively constant blower speed.

With such a controller or processor, the apparatus can be used for many different pressure treatment therapies, such as the pressure treatments for sleep disordered breathing, Cheyne-Stokes Respiration, obstructive sleep apnea (e.g., CPAP, APAP, Bi-Level CPAP, AutoVPAP), etc., or combinations thereof by adjusting a suitable pressure delivery equation. For example, the pressure treatment therapies of the devices described in U.S. Pat. Nos. 6,532,957, 6,845,773 and 6,951,217, which are incorporated herein by reference in their entireties, may be implemented with a apparatus 100 of the present technology. For example, as described in these patents, the controller and flow generator may be configured to provide pressure support ventilation. Such a treatment may ensure delivery of a specified or substantially specified target ventilation, for example, a minute ventilation, a gross alveolar ventilation or a alveolar ventilation, to the patient interface during the course of a treatment session by comparing an measure of ventilation with the target ventilation; or delivery of a tidal volume by comparing a measure of tidal volume with a target tidal volume. Thus, if a patient's respiration causes the measured ventilation to fall below or rise above the target ventilation over time, the flow generator will compensate with an increase or decrease respectively in the supplied pressure support ventilation. This may be accomplished with pressure variations that provide a bi-level form of therapy or some other form of therapy that may more smoothly replicate changes in a patient's respiration cycle. While the form of FIG. 10 illustrates a flow generator for generating such pressure support ventilation, as described herein, in some cases a apparatus may be implemented for monitoring without a flow generator for a pressure treatment.

Optionally, the apparatus 100 may also include additional diagnosis sensors 112 that may be contact or non-contact sensors. For example, the device may include an oximeter. The oximeter may generate a signal representative of a blood oxygen level of a patient. A suitable example oximeter or monitor device may optionally be any of the devices disclosed in International Patent Application No. International Application No. PCT/AU2005/001543 (Pub. No. WO/2006/037184) or International Patent Application No. PCT/AU1996/000218 (Pub. No. WO/1996/032055), the disclosures of which are incorporated herein by cross-reference. As disclosed in these incorporated PCT applications, the monitor may serve as diagnosis sensors that can also optionally provide a blood pressure and/or heart or pulse rate monitor for measuring a heart rate and/or blood pressure of the patient.

In some forms, the diagnosis sensors may also include an ECG monitor. Such a device may be configured to detect cardiac-related characteristics such as a heart rate and may also determine respiratory parameters (such as central or obstructive apneas, hypopneas, etc.) Optionally, these parameters may be determined by the analysis algorithms of controller 104 based on transmission of the ECG data to the controller or they may be determined by the monitor and be transmitted to the controller 104.

In some forms, the diagnosis sensors may include a movement sensor. For example, a suprasternal notch sensor or chest band may be implemented to generate a movement signal that is indicative of patient effort during respiration. Other suitable sensors may include the movement sensing devices disclosed in International Patent Application No. PCT/AU1998/000358 (Pub. No. WO1998/052467), the disclosure of which is incorporated herein by cross-reference. The movement sensors thus may provide a measure of patient effort and/or respiration rate and may be used as an alternative to a flow sensor or in conjunction with other flow sensors as discussed in more detail herein.

Some forms may monitor respiratory parameters with non-contact infrared or wireless biomotion sensors. One such example is the BiancaMed Doppler device which uses low power pulses of radio frequency energy transmitted and reflected back to a sensor to detect respiration rate, heart rate and movement, etc. Alternatively, or in addition thereto, contact respiratory monitoring devices such as a respiratory band or movement sensitive bed may be implemented to monitor patient respiratory parameters.

The signals from the sensors may be sent to the controller 104. Optional analog-to-digital (A/D) converters/samplers (not shown separately) may be utilized in the event that supplied signals from the sensors are not in digital form and the controller is a digital controller. Based on the signals from the sensor(s), the controller assesses the condition of the patient.

The controller may optionally include a display device 116 such as one or more warning lights (e.g., one or more light emitting diodes). The display device may also be implemented as a display screen such as an LCD or a touch sensitive display. Activation of the display device 116 will typically be set by the controller based on an assessment of the condition by the apparatus 100. The display device may be implemented to visually show information to a user of the apparatus 100 or a clinician or physician. The display device 116 may also show a graphic user interface for operation of the apparatus 100. User, clinician or physician control of the operation of the apparatus 100 may be based on operation of input switches 118 that may be sensed by the controller or processor of the apparatus.

Optionally, the controller may also include a communications device 120 for receiving and/or transmitting data or messages by the apparatus 100. For example, the communications device may be a wireless transceiver such as Bluetooth or WIFI transceiver. The communications device may also be a network communications device such as a phone modem and/or network card and may be implemented to send messages via the internet directly or through a computer to which the detection device may be docked. The communications device 120 may communicate with a remote device 122.

The controller 104 or processor 114 will typically be configured to implement one or more particular control methodologies such as the algorithms described in more detail herein. Thus, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. In still further forms, control over parameters of treatment may be set in accordance with a patient synchronization demand so as to permit a suitable treatment for mobility or exercise.

Some forms of the present technology involve an apparatus to generate pressure support ventilation. The apparatus may include at least one sensor adapted to measure at least one respiratory parameter and a flow generator adapted for coupling with a patient respiratory interface. The flow generator may be configured to provide a flow of breathable gas for pressure support ventilation to the patient respiratory interface. The apparatus may also include a controller coupled to the at least one sensor and the flow generator. The controller may be configured to control the pressure support ventilation with the flow generator. The controller may also be further configured with a rest mode and an exercise mode, the rest mode having a first value set of control parameters for the pressure support ventilation and the exercise mode having a second value set of control parameters for the pressure support ventilation.

In some cases, the controller may be configured to receive a user activated trigger stimulus, and, in response to the trigger stimulus to select the second value set of control parameters for the exercise mode. In response to the trigger stimulus, the controller may set a target respiratory control parameter as a function of a presently detected respiratory parameter sensed with the sensor. The target respiratory control parameter may be a target respiratory rate and the detected respiratory parameter may be a measured respiratory rate. The target respiratory control parameter may be a target ventilation and the detected respiratory parameter may be a measure of ventilation. Optionally, the target ventilation may be a target tidal volume and the measure of ventilation may be a measure of tidal volume. Still further, the target ventilation may be a target minute ventilation and the measure of ventilation may be a measure of minute ventilation. In some cases, the second value set of control parameters may comprise an increase in target values with respect to the first value set of control parameters.

Optionally, the apparatus may further include at least one user accessible button to activate the controller such that the button may be configured for actuating the trigger stimulus. Still further, the apparatus may also include a diaphragm electromyogram sensor to activate the controller such that the sensor may be configured for actuating the trigger stimulus. In some cases, the apparatus may include a vagal nerve sensor to activate the controller such that the sensor may be configured for actuating the trigger stimulus.

In some cases, the controller of the apparatus may be further configured with a cool down mode, and configured to receive another user activated trigger stimulus to initiate the cool down mode. The cool down mode may include a third value set of control parameters for the pressure support ventilation. The controller may be configured such that a value of the control parameters of the cool down mode may be varied from a respective value of the control parameters of the exercise mode toward a respective value of the control parameters of the rest mode. The controller may be configured such that a value of the control parameters of the cool down mode may be ramped from a respective value of the control parameters of the exercise mode toward a respective value of the control parameters of the rest mode.

Some forms of the present technology may involve a method for control of pressure support ventilation. The method may include measuring at least one respiratory parameter with a sensor. It may also include generating pressure support ventilation with a flow generator adapted for coupling with a patient respiratory interface. It may further include controlling, with a processor, the pressure support ventilation in a rest mode and an exercise mode. The rest mode may have a first value set of control parameters for controlling the pressure support ventilation and the exercise mode may have a second value set of control parameters for controlling the pressure support ventilation.

The method may further include receiving a user activated trigger stimulus, and, in response to the trigger stimulus, selecting the second value set of control parameters for the exercise mode. The method may also include, in response to the trigger stimulus, setting a target respiratory control parameter as a function of a presently detected respiratory parameter sensed with the sensor. The target respiratory control parameter may be a target respiratory rate and the detected respiratory parameter may be a measured respiratory rate. The target respiratory control parameter may be a target ventilation and the detected respiratory parameter may be a measure of ventilation. The target ventilation may be a target tidal volume and the measure of ventilation may be a measure of tidal volume. The target ventilation may be a target minute ventilation and the measure of ventilation may be a measure of minute ventilation. The second set of control parameters may include an increase in target values with respect to the first value set of control parameters. In some such methods, a user accessible button actuates the trigger stimulus. In some such methods, a diaphragm electromyogram sensor actuates the trigger stimulus. Still further, in some such methods, a vagal nerve sensor actuates the trigger stimulus.

Optionally, the methods may also include controlling pressure support ventilation in a cool down mode in response to receiving another user activated trigger stimulus, the cool down mode may have a third value set of control parameters for the pressure support ventilation. In some cases, a value of the control parameters of the cool down mode may be varied from a respective value of the control parameters of the exercise mode toward a respective value of the control parameters of the rest mode. In some cases, a value of the control parameters of the cool down mode may be ramped from a respective value of the control parameters of the exercise mode toward a respective value of the control parameters of the rest mode.

In some forms, the apparatus 100, such as when implemented to provide a pressure treatment to patient suffering respiratory insufficiency, COPD or other similar ailments, may serve to enhance physical activity or mobility for a patient. For example, the apparatus may be implemented to provide non-invasive ventilation to provide respiratory support for patients during mobility. Such a non-invasive ventilation may enhance exercise capacity in COPD patients or emphysemic patients. Thus, in some forms, a pressure treatment methodology, such as a control algorithm for non-invasive pressure support ventilation, may be implemented to promote exercise or patient mobility with suitable pressure support modes.

As a COPD patient gradually, exercises, their tidal volume and respiratory rate will increase. When the patient then rests, the tidal volume and respiratory rate decreases. In some forms of the present technology, a patient-responsive non-invasive ventilation methodology of the apparatus may be configured to adapt to patients' varying respiratory needs during exertion or exercise.

Accordingly, FIG. 11 illustrates an example of a methodology of a controller for such an apparatus. During use, the controller will generally permit a change to pressure support control parameters, such as an increase in ventilation (e.g., tidal volume) and respiratory rate at levels, that are suitable for exercise or mobility up to a maximum ventilation, such as a minute ventilation, and/or maxium respiratory rate so as to provide pressure support at those levels. In order to achieve the desired levels, the apparatus may be configured to respond to a user or patient stimulus for setting the synchronization of the apparatus with the patient's exercise requirements.

For example, the apparatus may provide NIV at initial levels in a rest mode to provide a pressure support suitable for a patient at rest at 400. Thus, the apparatus may begin treatment by accessing stored values of target parameters for the rest mode where those values of the target parameters are suitable for controlling ventilation or pressure support for patient rest. The user or patient may then begin to exercise. During exercise or shortly before, the patient may then provide a stimulus, such as executing a trigger, to initiate a modification procedure of the apparatus so that the apparatus may begin an exercise mode at 401. The modification procedure permits the values of the target parameters of the pressure support to be modified or set such that the pressure support will be provided at more suitable levels (e.g., increases in target ventilation (e.g., minute ventilation or tidal volume) or in target respiratory rate, or in the maximum or minimum values suitable for controlling pressure support) for exercise at 402. Thus, the modification procedure of the exercise mode may allow enforcement of different minimum and/or maximum values and/or target values of respiratory control parameters in the exercise mode at 403 from the rest mode.

In some such forms, the triggered change or, increase to the values of the control parameters of the pressure support ventilation for the exercise mode may optionally be predetermined. In such a case, the executed trigger may result in the apparatus accessing one or more stored values for the control parameters for the pressure support where the stored values of the control parameters are associated with the exercise mode. Such target, minimum and/or maximum values may be previously entered by a physician or clinician. For example, a respiratory rate target or ventilation target may be set as a physician selectable proportional function of the values of the control parameters of the rest mode so as to permit a proportional increase (or decrease) of the parameters from the rest mode. Optionally, in some forms, some of the values of the control parameters of the pressure support ventilation of the exercise mode may be learned so as to better synchronize with the level exercise of the user or patient. For example, the apparatus may learn the exercise respiratory rate, minute ventilation and/or tidal volume of the patient during an initial exercise period of the exercise mode or in response to a stimulus signal of the patient, such as by measuring these parameters from a flow signal in the initial period. Thereafter, such learned values may then be set for the control parameters of a later time period of the exercise mode.

In some forms, the stimulus for entering the exercise mode or making an adjustment to target values to accommodate the patient's state of exercise may be made by the patient by pressing a button of the treatment apparatus or a button on a remote control (e.g., a wired, wireless or infrared transmitter to transmit to an exercise mode signal or exercise synchronization signal to a receiver of the apparatus). Alternatively, the stimulus signal may be a detected physiological stimulus such as for example, a signal from a diaphragm electromyogram sensor, a signal from a sensor that is responsive to activation of the vagal nerve e.g. an oximeter, or an evaluation of a signal from a flow sensor.

In some forms, as further illustrated in FIG. 11, the apparatus may be configured to receive additional stimulus signals or executed triggers from the patient as the exercise progresses or cools down in or from the exercise mode. For example, with each additional stimulus signal, a new set of control values may be established. For example, at 404 a patient or user may trigger learning or loading of a further set of values for the control parameters. The new targets may then be set as the control parameters for the delivery of the pressure support ventilation at 405. The apparatus 100 may then control the pressure support in accordance with the new settings at 403. Each set of control values may be higher or lower than the previous control values based on an increase or decrease of activity.

For example, in some forms, the exercise mode may have a predetermined time interval, such as a maximum time set by a physician or clinician. In some such forms, a timer may begin when the exercise mode starts and the mode may terminate when a preset maximum time is reached. During the exercise mode, the apparatus may deliver pressure support ventilation with the exercise mode control values that are suitable for patient exercise. At the conclusion of the exercise mode, the apparatus may switch to the rest mode, so as to deliver pressure support ventilation with the rest mode control values that are suitable for patient rest. Optionally, the apparatus or remote control may include a button to terminate the exercise mode before the maximum time is reached.

Still further, in some forms, the termination of the exercise mode may initiate a cool down mode. During the cool down mode, the values of the control parameters may be varied over a selectable period of time. For example, the values may be ramped from the values of the target parameters of the exercise mode to the values of the target parameters of the rest mode. For example, the respiratory rate and/or ventilation targets may be automatically modified so as to ramp down or be gradually stepped down over a period of time to the rest mode values.

5.4 OTHER ASPECTS

The present technology may be packaged as an exercise module or accessory to be used with a range of different ventilators.

Preferably the parameters that are adjustable by the patient are adjustable within limits. Such limits may be established by a clinician prior to use by the patient.

5.5 ADVANTAGES

One advantage of the present technology is that it allows ventilators to more closely match a patient's need, particularly in the face of a changing need, e.g. increasing or decreasing, such as when a patient attempts to exercise.

An advantage of the present technology is that it is easier and more comfortable for patients to use when compared to a ventilator that may have one fixed setting of e.g. minute ventilation, or pressure support.

In addition, the present technology allows a patient to pre-empt a need for a sooner breath, or an increased level of support. By pressing on the relevant button momentarily before they require a breath, the system can respond just as the patient actually needs the breath.

5.6 REFERENCE SIGNS LIST apparatus 10
ventilator 12
button 14
pc 16
digital communication interface 18
inflection point 17
pressure support 19
Pathway 21
Apparatus 100
Patient respiratory interface 102
Controller 104
Blower 105
Pressure sensor 106
Flow sensor 107
Mask 108
Delivery tube 110
Additional diagnosis sensors 112
Processor 114
Display device 116
Input switches 118
Communications device 120
Remote device 122
Patient interface 3000
pap device 4000
external housing 4010
panel 4015
chassis 4016
handle 4018
pneumatic block 4020
pneumatic component 4100
inlet air filter 4112
blower 4142
pressure sensor 4152
flow sensor 4154
Air circuit 4170
electrical component 4200
PCBA 4202
power supply 4210
input device 4220
processor 4230
clock 4232
pressure device controller 4240
protection circuit 4250
memory 4260
transducer 4270
flow transducer 4271
pressure transducer 4272
Oximeter 4273
Electromyograph 4274
output device 4290
algorithm 4300
humidifier 5000

5.7 OTHER REMARKS

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A controller for a ventilator, the ventilator being configured to deliver a pressure support waveform to a patient, said pressure support waveform having an inspiratory phase and a subsequent expiratory phase, and the controller being configured to adjust an expiratory pressure during the expiratory phase in response to an indication of a change in metabolic demand of the patient, wherein the controller is configured so that in response to an increase in a level of metabolic demand up to a predetermined limit of metabolic demand, the controller increases a level of the expiratory pressure to a level no higher than a maximum expiratory pressure value, and wherein the controller is further configured so that in response to an increase in the level of metabolic demand above the predetermined limit of metabolic demand, the controller increases a level of inspiratory positive pressure while a level of expiratory positive air pressure will remain substantially constant at the maximum expiratory pressure value.

2. The controller of claim 1, wherein the controller is further configured to accept a signal from a metabolic demand responsive transducer, and to determine a state of metabolic demand from said metabolic demand responsive transducer.

3. The controller of claim 2, wherein said metabolic demand responsive transducer is an oximeter.

4. The controller of claim 2, wherein said metabolic demand responsive transducer is a flow sensor.

5. The controller of claim 2, wherein said metabolic demand responsive transducer is a diaphragm electromyograph.

6. The controller of claim 2, wherein said metabolic demand responsive transducer is a combination of a flow sensor and an electromyograph.

7. The controller of claim 1, configured to increase an inspiratory pressure at a first rate in response to an increase in metabolic demand up to a given point.

8. The controller of claim 7, configured to increase an inspiratory pressure at a second rate in response to an increase in metabolic demand above the given point.

9. The controller of claim 8 wherein the second rate is lower than the first rate.

10. The controller of claim 1 wherein a maximum expiratory pressure value at the given point is about 10 cmH$_2$0.

11. The controller of claim 1 configured to follow a predetermined pressure support pathway.

12. The controller of claim 1, wherein at least for a range of metabolic demand values, the controller is configured to linearly adjust the at least one parameter of the ventilator in response to a change in metabolic demand values in the range.

13. The controller of claim 1, wherein at least for a range of metabolic demand values, the controller is configured to discretely adjust between metabolic demand values in the range.

14. The controller of claim 1, wherein the indication of change in metabolic demand is input manually.

15. The controller of claim 1, wherein the indication of change in of metabolic demand is determined automatically.

16. A ventilator for providing ventilatory support to a patient, the ventilator comprising:
   a power supply;
   a controller as claimed in claim 1; and
   a pressure device under the control of the controller.

17. Apparatus for providing ventilatory assistance to a patient to assist in exercising comprising a ventilator as claimed in claim 16, and a metabolic demand responsive transducer.

18. A controller for a ventilator, the ventilator being configured to deliver a pressure support waveform to a patient, said pressure support waveform having an inspiratory phase and a subsequent expiratory phase, and the controller being configured to adjust an expiratory pressure during the expiratory phase in response to an indication of a change in metabolic demand of the patient, wherein the controller is configured so that in response to an increase in a level of metabolic demand up to a first metabolic demand threshold, the controller increases a level of the expiratory pressure to a level no higher than a maximum expiratory pressure value, and wherein the controller is further configured so that in response to an increase in the level of metabolic demand above the first metabolic demand threshold, the controller increases a level of inspiratory positive pressure while a level of expiratory positive air pressure will remain substantially at the maximum expiratory pressure value.

19. A method of control of a ventilator, the ventilator being configured to deliver a pressure support waveform to a patient, said pressure support waveform having an inspiratory phase and a subsequent expiratory phase, the method comprising:
   adjusting with a processor an expiratory pressure during the expiratory phase in response to an indication of a change in metabolic demand of the patient, so that in response to an increase in a level of metabolic demand up to a predetermined limit of metabolic demand, a level of the expiratory pressure increases to a level no higher than a maximum expiratory pressure value, and so that in response to an increase in the level of metabolic demand above the predetermined limit of metabolic demand, a level of inspiratory positive pressure increases while a level of expiratory positive air pressure will remain substantially constant at the maximum expiratory pressure value.

20. The method of claim 19, further comprising with the processor, accepting a signal from a metabolic demand responsive transducer and determining a state of metabolic demand from said metabolic demand responsive transducer.

21. The method of claim 20, wherein said metabolic demand responsive transducer is an oximeter.

22. The method of claim 20, wherein said metabolic demand responsive transducer is a flow sensor.

23. The method of claim 20, wherein said metabolic demand responsive transducer is a diaphragm electromyograph.

24. The method of claim 20, wherein said metabolic demand responsive transducer is a combination of a flow sensor and an electromyograph.

25. The method of claim 19, further comprising with the processor increasing an inspiratory pressure at a first rate in response to an increase in metabolic demand up to a given point.

26. The method of claim 25, further comprising with the processor increasing an inspiratory pressure at a second rate in response to an increase in metabolic demand above the given point.

27. The method of claim 26 wherein the second rate is lower than the first rate.

28. The method of claim 19 wherein a maximum expiratory pressure value at the given point is about 10 cmH$_2$0.

29. The method of claim 19 further comprising with the processor following a predetermined pressure support pathway.

30. The method of claim 19, wherein at least for a range of metabolic demand values, linearly adjusting with the processor the at least one parameter of the ventilator in response to a change in metabolic demand values in the range.

31. The method of claim 19, wherein at least for a range of metabolic demand values, discretely adjusting with the processor between metabolic demand values in the range.

32. The method of claim 19, wherein the indication of change in metabolic demand is input manually to the processor.

33. The method of claim 19, wherein the indication of change in metabolic demand is determined automatically by the processor.

* * * * *